United States Patent [19]

Cole et al.

[11] Patent Number: 5,990,094
[45] Date of Patent: Nov. 23, 1999

[54] INHIBITORS OF SOROTONIN N-ACETYLTRANSFERASE

[75] Inventors: Philip A. Cole, New York; Ehab Khalil, Bronx, both of N.Y.

[73] Assignee: The Rockefeller University, New York, N.Y.

[21] Appl. No.: 09/014,340

[22] Filed: Jan. 27, 1998

[51] Int. Cl.[6] .............................. A61K 31/70; C07H 19/20
[52] U.S. Cl. ........................................ 514/47; 536/26.23
[58] Field of Search ........................ 514/47; 536/26.13, 536/26.23

[56] References Cited

PUBLICATIONS

Albert et al, 1992, Proc Natl Acad Sci USA, 89:12053–7.
Arendt et al, 1992, Br J Psych, 161:361–4.
Borjigin et al, 1995, Nature, 378:783–85.
Cole et al, 1994, J Biol Chem, 269:30880–7.
Coon et al, 1995, Science, 270:1681–3.
DeAnglis et al. (1998) J. Biol. Chem.: in print ??????.
D'Sa et al, 1996, J Neurochem, 67:900–6.
Ishida et al, 1987, J Biol Chem, 262:2895–9.
Kim et al, 1997, J Am Chem Soc, 119:11096–7.
Klein et al, 1996, Trends Endocrin Metab, 7:106–12.
Klein et al, 1997, Recent Progress in Hormone Reseachm 52:307–57.
Meikle et al, 1995, Biochem J, 308:327–33.
Nguyen et a, 1984, Hoppe–Seyler;s Z Physiol Chem, Bd. 365–:1–8.
Redman et al, 1983, Science, 219:1089–91.
Reppert et al, 1994, Neuron, 13:1177–85.
Reppert et al, 1995, Proc Natl Acad Sci USA, 92:8734–8.
Voisin et al, 1984, J Biol Chem, 259:10913–8.
Yang et al, 1996, Nature, 382:319–24.

*Primary Examiner*—Gary L. Kunz
*Attorney, Agent, or Firm*—Klauber & Jackson

[57] ABSTRACT

This invention is directed to a compound having the formula I.

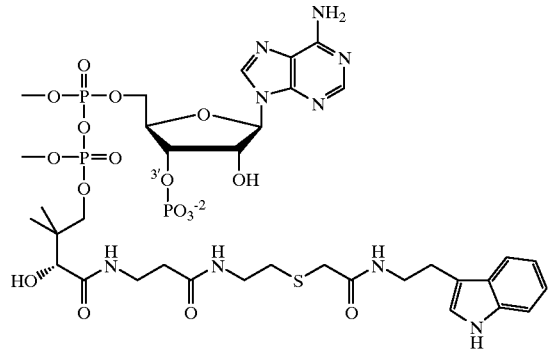

This invention is directed to a pharmaceutical composition comprising a compound which inhibits serotonin N-acetyltransferase having the formula I and a pharmaceutical acceptable carrier. The present invention relates to novel compounds and analogs which inhibit the serotonin N-acetyltransferase enzyme, and to processes for their preparation.

6 Claims, 22 Drawing Sheets

INHIBITORS OF SOROTONIN N-ACETYLTRANSFERASE

BACKGROUND OF THE INVENTION

This invention relates generally to novel compounds which inhibit the serotonin N-acetyltransferase enzyme, modulate the serotonin-melatonin pathway and various methods of use for the compounds of the invention.

The enzyme serotonin N-acetyltransferase, is responsible for the daily rhythmic cycle of melatonin in animals and man. Hormonal influences over circadian rhythm are currently poorly understood. While a wide array of hormones are known to cycle throughout the day, their precise roles in the physiology of the sleep/wake cycle have remained elusive. The hormone melatonin (5-methoxy-N-acetyltryptamine) is hypothesized to play an important role in the regulation of circadian rhythm. Discovered in 1917 as an extract of pineal gland which could lighten frog skin (1), melatonin's structure was not elucidated until 1959 by Aaron Lerner (2,3). Subsequently, its serum levels were found to cycle with diurnal periodicity, rising 10–100 times its daytime levels at night (FIG. 1) (4). What melatonin is really doing and how it is doing in both animals and man remain mysterious (5).

The circadian clocks in living organisms are thought to regulate basal body temperature, locomotor activity, sleep, eating behavior, and hormone production (5). In non-mammalian vertebrates, the pineal gland is the principal regulator of the circadian clock (6). In mammals including humans, the brain's suprachiasmatic nucleus (SCN) is believed to contain the "master clock" with outputs to and inputs from the pineal gland (5–7). The current model is that the suprachiasmatic nucleus sends outputs via the noradrenergic pathway to regulate pineal gland activity and the SCN contains melatonin receptors which allow for pineal gland input (FIG. 2) (5).

Serotonin is the most abundant hormone produced in the pineal, and the pineal is its site of highest concentration in the brain (5,6). Serotonin is a hormone-neurotransmitter with hypothesized roles in physiologic processes such as sleep and in pathophysiologic conditions including depression, chronic pain, and migraine, and drug addiction (8). Three major classes of clinical anti-depressant agents are thought to achieve their effect by stimulating the serotonin pathway, including monoamine oxidase inhibitors (e.g. deprenyl), tricyclic antidepressants (e.g. imipramine), and serotonin re-uptake inhibitors (e.g. prozac) (8). It is not currently known to what extent pineal-derived serotonin contributes to serotonin's overall physiological effects in man.

Serotonin is a biosynthetic precursor of melatonin and the pineal is the principal source of melatonin in the body (5,6). Despite significant investigation, melatonin's physiologic roles are not yet well understood. Melatonin's primary function is suggested to be entrainment of circadian rhythm in response to changes in external light (5). In this role, melatonin would be important in temperature regulation, mood, and the sleep-wake cycle (5, 9, 10). Solid evidence has also been obtained for melatonin's role in reproductive fitness in mammals (11, 12). More speculative claims have been advanced concerning melatonin's possible roles in effecting the immune, cardiovascular, and gastro-intestinal systems and in playing a role in cancer, aging, anorexia, and psychiatric disorders (Table 1). There is relatively little hard experimental evidence to validate or refute these claims at present (25).

Studies involving pinealectomy and those involving exogenous melatonin administration to discern melatonin's function have been reasonably compelling in confirming melatonin's role in circadian rhythm regulation in mammals. Pinealectomized rats maintained in constant light show a major disruption in wheel-running activity compared to controls (26). Exogenous melatonin administration has been shown to cause phase shifting in rat activity as well as in humans (27, 28). An intact SCN appears necessary for melatonin's entrainment effects.

In keeping with melatonin's role as a central nervous system hormone, receptor binding sites have been reported in discrete regions of the mammalian brain. These binding sites were classified as G-protein coupled receptors on the basis of pertussis-toxin sensitive adenylyl cyclase inhibition and affinity modulation by guanine nucleotides (29). In the last 3–4 years, two mammalian melatonin receptors have been identified by expression cloning and shown to have expression patterns consistent with their predicted locations from hormone binding studies (30, 31). High concentrations of receptor nRNAs have been detected in the suprachiasmatic nucleus of the hypothalamus and the hypophyseal pars tuberalis.

In addition, there are recent reports of intracellular receptors for melatonin. These receptors are "orphan" members of the steroid hormone/Zn-finer DNA binding family (32, 33). The $K_d$ of melatonin binding and activation appears to be considerably higher, 10–100 fold compared to that of the G-protein family, and their physiologic relevance is still unclear.

Melatonin is routinely purchased at over the counter drug and health-food stores and used by many individuals to attempt to relieve jet lag, insommia, loss of vitality with aging, problems with shift work, and affective disorders. The oral bioavailability in people is reportedly quite variable (25-fold range, refs. 5, 34). Even with the lower doses that are sold (5–10 mg), this can drive serum levels hundreds of times higher than physiologic night-time serum levels (ca 500 pM) Consequently, effects that are observed may be due to alternative signalling pathways than the normal endogenous melatonin-responsive pathways. While there are currently no reported toxic effects of pharmacologic melatonin dosing (300 mg/d, the melatonin content of about 1.5 million pineal glands is approved for clinical trials), the long-term effects of massive doses of melatonin are relatively unexplored (5).

The biosynthesis of melatonin begins with L-tryptophan (Table 2). This naturally occurring amino acid is present in the diet and uptake by the brain is dependent on specific transport mechanisms. The first step in melatonin biosynthesis is hydroxylation of the tryptophan indole ring at the 5-position to afford 5-hydroxytryptophan. This step is rate-limiting in serotonin production and is catalyzed by the mitochondrial enzyme non-heme iron monooxygenase, tryptophan hydroxylase (36). The second step leading to serotonin (5-hydroxytryptamine) is catalyzed by the cytoplasmic enzyme aromatic amino acid decarboxylase (37). This pyridoxal-dependent enzyme effects decarboxylation of L-dopa as well as 5-hydroxytryptophan in a constitutive fashion in the pineal. The conversion of serotonin to N-acetylserotonin, the immediate precursor of melatonin is highly regulated in the pineal and is catalyzed by serotonin N-acetyltransferase (arylalkylamine N-acetyltransferase, AANAT) (FIG. 3) (38). Daytime levels of AANAT are up to 100-fold lower than nighttime levels in mammalian pineal glands, and it is this enzyme which is essentially fully responsible for the nighttime surge in melatonin production and drop in pineal serotonin (FIG. 4) (39, 40). The enzyme is acetyl-CoA dependent, and unlike the other enzymes in the pathway, had eluded characterization until very recently because of its instability and low abundance (41, 42). The final enzyme in melatonin biosynthesis is hydroxyindole-O-methyltransferase (HIOMT), a constitutive enzyme present in the pineal. HIOMT utilizes S-adenosylmethionine to effect O-methylation of the 5-hydroxy function of N-acetylserotonin (43). This enzymatic step appears to be minimally regulated and in most circumstances is not rate-limiting for melatonin production (5, 40).

AANAT activity was discovered in the early 1960's by Julius Axelrod (44). In 1970, Klein and Weller showed that this enzyme activity was regulated in a day/night cycle in the pineal gland and was primarily responsible for the day/night rhythm of melatonin (FIG. 4) (39, 40). Later, the enzyme was shown to be different from arylamine N-acetyltransferase, which is also present in the pineal (38). Because of its low abundance and instability, few mechanistic studies on the enzyme have been reported. Unlike the other enzymes involved in melatonin biosynthesis, no potent or specific inhibitors of AANAT have been reported.

In 1995, AANAT was cloned after many years of effort (41, 42). It is a 24 kDa (207 amino acids in length) protein with amino acid sequence highly conserved from chicken to man, showing>80% amino acid identity between species (45, 46). Although AANAT shows little homology to other genes in the data bank, it does contain 2 short C-terminal regions (ca. 10–20 aa each) called motifs A (amino acids 121–140) and B (amino acids 165–177) which mark AANAT as a member of a superfamily of proteins (>150 members so far identified, E. Koonin, NIH, private communication) that are believed to be largely composed of acetyl-CoA dependent transferase (45). Included in this family appear to be at least one member (PCAF) of the histone acetyltransferases (HATs) involved in the regulation of gene transcription (50). Very little is known about the substrate selectivity, mechanism, or inhibition of this enzyme family.

OBJECTS OF THE INVENTION

It is an object of the present invention to provide novel compounds and analogs which inhibit the serotonin N-acetyltransferase enzyme, which have a variety of utilities.

It is a further object of the present invention to provide processes for the preparation of the aforesaid compounds, and their salts under favorable conditions in large quantities.

A still further object of the present invention is to provide methods for using the novel compounds. These methods include a variety of applications, both industrial and medical, which result from the properties of the aforesaid compounds.

It is thus a further object of the present invention to provide methods of using the compounds of the instant invention for revealing biologic function of melatonin and pineal serotonin.

It is a further object of the present invention to provide compounds useful in regulating serotonin and melatonin.

Another object of the present invention is to utilize the compounds of the present invention as fluorescent tags for biomolecules, so as to enable the labeling of such molecules and the monitoring of the disposition of such molecules by the mammalian body.

A still further object of the present invention involves the use of the compounds of the present invention as components of kits for use in assaying biomolecules tagged with the aforesaid compounds.

SUMMARY OF THE INVENTION

This invention is directed to a pharmaceutical composition comprising an inhibitor a 11.1 serotonin N-acetyltransferase and analogs thereof and a pharmaceutical acceptable carrier. Further, this invention is directed to a compound having formula I.

The present invention relates to novel compounds and analogs which inhibit the serotonin N-acetyltransferase enzyme, and to processes for their preparation. More particularly, this invention concerns compounds represented by the formulas II–VI.

DETAILED DESCRIPTION OF THE INVENTION

Figure 1:
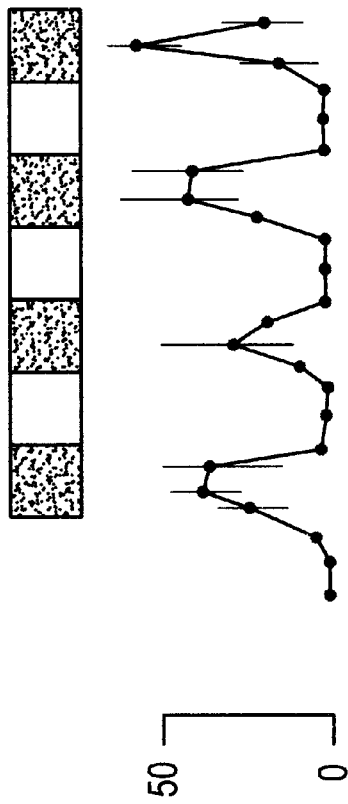
FIG. 1. Daily Plasma Melatonin Cycle (averaged from 5 men)

The lower alkyl groups referred to herein preferably contain 1–6 carbon atoms and include methyl, ethyl, propyl, butyl, pentyl, hexyl, and the corresponding branched-chain isomers thereof. These groups are optionally substituted by one or more halo, hydroxy, amino or lower alkylamino groups.

Where the possibility exists for substitution of a phenyl or aryl ring, the position of the substituents may be ortho, meta, or para to the point of attachment of the phenyl or aryl ring to the nitrogen of the hydrazine group. Preferably, the substituents are para or meta to the point of attachment, and where more than one is present on the same ring, they are preferably in the para and meta positions.

The halo atoms in the above formula may be fluoro, chloro, bromo or iodo. The lower alkoxy groups contain 1–6, and preferably 1–3, carbon atoms and are illustrated by methoxy, ethoxy, n-propoxy, isopropoxy and the like.

This invention is directed to a pharmaceutical composition comprising an inhibitor a serotonin N-acetyltransferase and analogs thereof and a pharmaceutical acceptable carrier. This invention is directed to a pharmaceutical composition comprising an inhibitor a serotonin N-acetyltransferase containing tryptamine and acetyl-CoA and a pharmaceutical acceptable carrier.

This invention is directed to a compound having formula I.

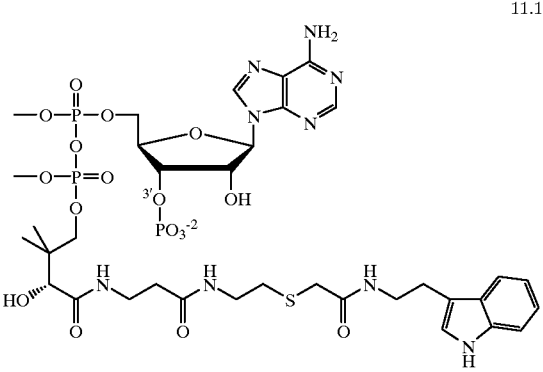

11.1

This invention is directed to a pharmaceutical composition comprising a compound which inhibits serotonin N-acetyltransferase having the formula I and a pharmaceutical acceptable carrier.

The present invention relates to novel compounds and analogs which inhibit the serotonin N-acetyltransferase enzyme, and to processes for their preparation. More particularly, this invention concerns compounds of the formula V

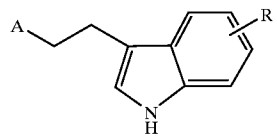

wherein A is a halogen, hydroxy or alkyl;

R' is a halogen, hydroxy or alkyl.

The distance between the indole and coenzyme A of formula I may be varied from two to six carbons and contain alkyl chains. Also, an oxygen atom may be substituted in all the carbon linkers. In order to introduce rigidity the compound may be tethers by alkyl substitution or cyclization. It is further contemplated that the nitrogen atom of the amine substrate may optimally be positively charged for binding. Thus increased affinity may be obtained by eliminating the carbonyl oxygen from the linker as exemplified by analog 20.1.

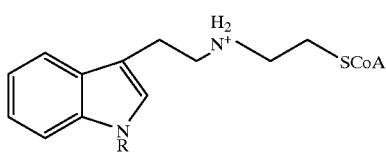

20.1

It is contemplated that to mold the tether into a tetrahedral transition state mimic in order to obtain compounds 21.1 and 22.1.

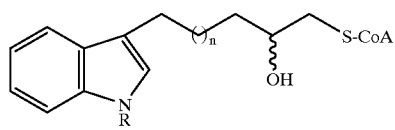

21.1

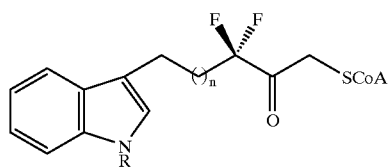

22.1

It is contemplated by this invention to substitute for tryptamine the following analogs: 6-fluorotryptamine, 5-methyltryptamine, Nw-methyltryptamine, and a-methyltryptamine; or other large hydrophobic molecules such as hydrophobic -CoA analogs and phenethylamine.

This invention provides the bisubstrate analog compound of formula 11.1 lacking the phosphate 23.1 and containing phosphopantetheine 23.2 and pantetheine 23.3. This

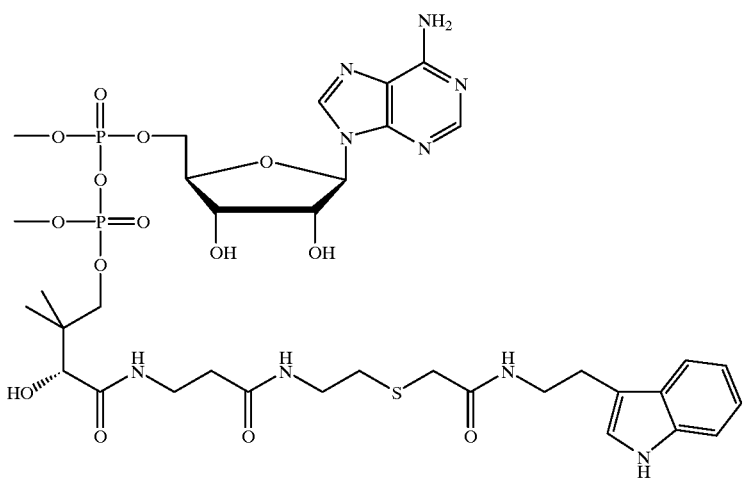

23.1

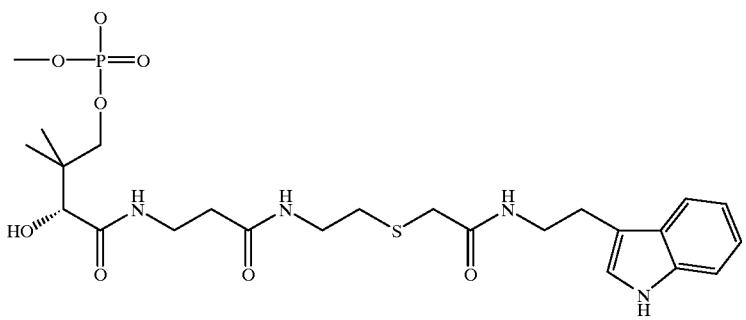

23.2

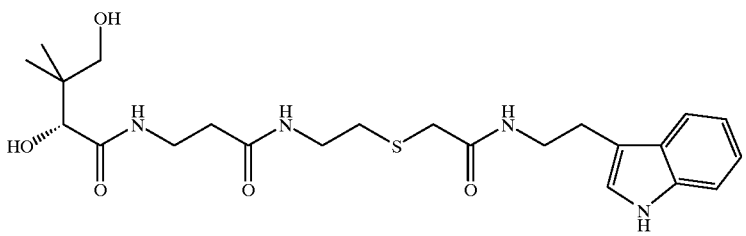

23.3

The compound represented by the formula V (23.1) may have A atomic group and R' which can be selected from the group of a halogen, hydroxy or alkyl.

The compound represented by the formula VI (23.3) may have A atomic group and R' which can be selected from the group of a halogen, hydroxy or alkyl and B being an alkyl tether to adenosine or a tether.

The compounds of this invention biologically and pharmaceutically acceptable and may contain salts wherein the $X^-$ anion is derived from a acid. The resultant salts can thus be derived from a variety of organic and inorganic acids such as sulfuric, phosphoric, hydrochloric, hydrobromic, sulfamic, citric, lactic, maleic, succinic, tartaric, cinnamic, acetic, benzoic, gluconic, ascorbic, methanesulfonic and related acids.

Of the compounds encompassed by formula I, certain substituents are preferred. For instance, the compounds wherein both the A and R' groups are a halogen, hydroxy or alkyl are preferred.

Reaction conditions for the instant process vary depending upon the nature of the starting materials, and the presence or absence of a solvent. Where the various R,R''' and R''' substituents would allow side reactions, they can be suitably protected, prior to the conduct of the reaction, to avoid such reactions. Typical protecting groups useful for such procedures are well-known in the art, and can be removed after isolation of the compound.

The compounds of the instant invention possess valuable properties which make them useful in numerous commercial applications, both industrial, medical and therapeutic. Specifically, the compounds are useful for the inhibition of serotonin N-acetyltransferase.

Further the compounds are useful for the regulation of melatonin by administering the compound to a subject and thereafter administering melatonin in a suitable dosage so as to regulate melatonin in subject.

Further the compounds are useful for reducing the levels of melatonin in a subject by administering to a subject a pharmaceutical composition containing the compounds and a suitable carrier or buffer.

Further the compounds are useful for determining the biologic function of melatonin or pineal serotonin. This invention is directed to a method of determining whether a ligand can specifically bind to serotonin N-acetyltransferase. Further, this invention is directed to a method of screening drugs.

Further, the compounds are useful for the following: 1) temperature regulation; 2) aiding in sleep; 3) pubertal development; 4) aging; 5) reproduction; 6) immunosuppressing natural killer cell; 7) immunostimulating; 8) SIDS (sudden infant death syndrome; 9) cardiovascular disease; 10) liver disease; 11) seasonal affective disorder; 12) blindness; 13) anorexia; and 14) breast cancer.

The compounds of the instant invention possess interesting spectroscopic properties, especially fluorescent properties, which enable their use in a variety of commercial applications. For instance, the compounds can be used as fluoroscent dyes in a range of blue, red, green, yellow colors, and especially blue and green colors. The color of fluorescence may be different from the absorption color. They can be utilized directly for the dyeing of textiles, and/or may be incorporated into commercially available polymer matrices, in typically, but not limited to, an amount of about 1–3% by weight, based upon the polymer matrix. Preferred apolar polymer matrices are selected from the group consisting of polymethyl methacrylate, polystyrene, polybutadiene-modified polystyrene, polycarbonate, polyvinyl chloride and polyamide, with polymethyl methacrylate and polystyrene matrices being particularly preferred. Other polymer matrices which can also be used include polycondensates based upon urea and formaldehyde or polyamide. Such fluorescent pigments possess high luminenscence and advantageous application properties, for example, high lightfastness and a low migration tendency.

The possession of fluorescent properties further enables the use of the compounds of the instant invention in a variety of medical, pharmaceutical and diagnostic applications. The compounds of the instant invention can also be utilized to label various therapeutic agents to enable their disposition in the body. As such, therapy with such labeled therapeutic agents can be closely monitored with respect to target organs and tissues. This is particularly useful in the treatment of various cancers, especially those of a solid tumor type, where localization of the chemo-therapeutic agent is extremely important, and dosage, due to the possibility of side-effects, must be closely monitored.

DETAILED DESCRIPTION

EXAMPLE 1

Serotonin N-acetyltransferase (arylalkylamine N-acetyltransferase, AANAT, EC 2.3.1.87) is the penultimate enzyme in melatonin biosynthesis. This enzyme is of special biological interest because large changes of its activity drive the large night/day rhythm in circulating melatonin in vertebrates. In this study the kinetic mechanism of AANAT action was studies using bacterially expressed glutathione S-transferase (GST(-AANAT fusion protein. The enzymologic behavior of GST-AANAT and cleaved AANAT was essentially identical. Two-substrate kinetic analysis generated an intersecting line pattern characteristic of a ternary complex mechanism. The dead end inhibitor analog desulfo-CoA was competitive versus acetyl-CoA and noncompetitive versus tryptamine. Tryptophol was not an alternative substrate but was a dead end competitive inhibitor versus tryptamine and an uncompetitive inhibitor versus acetyl-CoA, indicative of an ordered binding mechanism requiring binding of acetyl-CoA first. N-Acetyltryptamine, a reaction product, was a noncompetitive inhibitor versus tryptamine and uncompetitive with respect to acetyl-CoA. Taken together these results support an ordered BiBi ternary complex (sequential) kinetic mechanism for AANAT and provide a framework for inhibitor design.

MATERIALS AND METHODS

Chemicals

The following were purchased: acetyl-CoA (Pharmacia Biotech Inc.); tryptamine-HCl, desulfo-CoA, glutathione-agarose, DTNB (Sigma); sodium phosphate, dithiothreitol, guanidinium-HCl, EDTA (Fisher Scientific); tryptophol (Aldrich); and [$^{14}$C]acetyl-CoA (60 Ci/mol) (NEN Life Science Products). N-acetyltryptamine was synthesized by reacting tryptamine-HCl (500 mg, 2.5 mmol) with acetic anhydride (260 mg, 2.5 mmol) in the presence of excess triethylamine (1.75 ml). After vigorous stirring at room temperature for 50 min, the mixture was partitioned between ethyl acetate (80 ml) and water (70 ml). The organic phase was washed with saturated aqueous $NaHCO_3$ (50 ml), 0.1 M HCl (50 ml), $Na_2SO_4$ (anhydride), and the resultant was concentrated in vacuo to afford N-acetyltryptamine as off-white crystals (88% yield). Purity (>95%) was established by TLC and $^1$H NMR.

Expression and Purification

The entire open reading frame of the DNA encoding sheep AANAT in the plasmid vector pET15b (5) was excised with XhoI and religated in-frame into pGEX-4T-1 and transformed into the *Escherichio coli* strain BL21(DE3) pLysS. A frozen stock of this strain (10 μl) was used to inoculate 25 ml of Luria Broth containing ampicillin (100 μg/ml) and chloramphenicol (34 μg/ml) in a culture flask and grown overnight at 37° C. in a floor shaker. The culture was used to inoculate 2 liters of Luria Broth divided into three Erlenmeyer flasks also containing ampicillin (100 μg/ml) and chloramphenicol (34 μg/ml) (1:100 v/v) and grown at 37° C. in a floor shaker until the absorption at 595 nm was equal to 0.5–0.6. The flasks were cooled to room temperature by standing at 4° C. for 20 min. and then treated with isopropyl-1-thio-β-D-galactopyranoside (to a final concentration of 0.2 mM). The cultures were maintained at 24° C. for an additional 5 h. The cells were pelleted by centrifugation (4° C., 5,000×g, 10 min) and the cell paste (5.2 g) snap frozen with liquid $N_2$ and stored at -80° C. The cell paste was resuspended in 30 ml of lysis buffer (1×phosphate-buffered saline, 10 mM dithiothreitol, 10% glycerol, 10 mM EDTA, pH-6.9), and the suspension was lysed by passage through a French pressure cell at 12,000 p.s.i. Insoluble protein and cell debris were removed by centrifugation (4° C., 27,000×g, 30 min followed by 4° C., 100,000×g, 120 min), and the supernatant (25 ml) was snap frozen with liquid $N_2$ and stored at -80° C. The thawed mixture was then incubated with Nutator (Fisher Scientific), mixing with 2 ml of glutathione-agarose (100 mg of dried resin, swollen with 20 ml of $H_2O$, then pre-equilibrated in lysis buffer by washing two times with 10 ml, pelleting in a 50-ml centrifuge tube at 2,000×g in a swinging bucket centrifuge for 5 min) at room temperature for 30 min. The mixture was centrifuged at 2,000×g for 5 min and the supernatant carefully pipetted away. The pelleted resin was resuspended and washed two times with lysis buffer+263 mM NaCl (10 ml each) at 4° C. Subsequently, the glutathione-agarose resin was incubated at room temperature for 30 min on a Nutator with 20 ml of lysis buffer+113 mM MaCl+50 mM glutathione (whose pH was adjusted to 7 with 8 N NaOH). The resin was pelleted, and the supernatant (20 ml) was recovered and dialyzed (2×500 ml) at 4° C. against storage buffer (4.3 mM sodium phosphate, 1.4 mM potassium phosphate, 337 mM NaCl, 2.7 mM KCl, 5 mM dithiothreitol, 1 mM EDTA, 10% glycerol, pH 6.9). The protein concentration postdialysis was 0.5 mg/ml (total yield 10 mg) as determined by Bradford assay referenced to bovine serum albumin standard. Purity was approximately 90% as determined by 10% SDS-polyacrylamide gel electrophoresis (Coomassie staining). The protein was stored (-80° C.) at 0.5 mg/ml concentration or after Centricon (Amicon Inc., Beverly, Mass.) ultrafiltration, at 4.2 mg/ml, and maintained stable enzyme activity for at least 4 months.

The GST-AANAT fusion protein was cleaved with thrombin and then purified according to the manufacturer's instructions (Pharmacia) to produce GST-free AANAT and protein concentration determined by Bradford assay.

Enzyme Assays.

AANAT activity was measured primarily using a newly developed spectrophotometric assay. An established radiochemical assay was also used with minor modifications (12).
DTNB Product Detection Assay This assay is based on the detection of CoASH generated during acetyl transfer by reaction with the thiol reagent DTNB (19). This assay was typically performed using a buffer containing 0.05 M sodium phosphate, pH 6.8 500 mM NaCl, 2 mM EDTA, 0.05 mg/ml bovine serum albumin variable acetyl-CoA (0.1–3 mM), and variable tryptamine (0.05–1 mM) at 30° C. in 0.3 ml in 1.5-ml microcentrifuge tubes. Reactions were initiated with enzyme (3 μl, 5–30 nM final concentration) that had been prediluted (10–100 fold) in 50 mM sodium phosphate, 500 mM NaCl, 2 mM EDTA, and 0.05 mg/ml bovine serum albumin in the absence of reducing agent immediately before use and maintained on ice during the assay. The reactions were quenched for 0–3 min with 0.6 ml of a buffer containing guanidinium-HCl (3.2 M), sodium phosphate (0.1 M), pH 6.8. These mixtures were treated with 0.1 ml of DTNB (2 mM, 0.1 M sodium phosphate, pH 6.8, 10 mM EDTA), vortexed, and allowed to stand for 5 min before absorbance readings were performed at 412 nm (thiophenolate-quantified assuming $\epsilon=13.7\times10^3$ $M^{-1}$ $cm^{-1}$) (19). Background absorbances (with all components added including enzyme) were measured and subtracted from the total absorbance. A background correction was made for each acetyl-CoA concentration because acetyl-CoA had a small contaminant of free thiol (1–2% presumably free CoASH). The rate of conversion of acetyl-CoA to CoASH in the absence of amine was negligible over the course of the assay. Activity was linear with time for at least 3 min at high (2 mM) and low (0.1 mM) acetyl-CoA. Velocity measurements were made under initial conditions where reaction of the limiting substrate did not exceed 10%.
Radiochemical Assay A modification of an established radiochemical assay (12) was used in which the concentration of tryptamine (1 mM) is incubated with [$^{14}$C]acetyl-CoA (1 mM; specific activity= 1.24 ci/mol) and N.[$^{14}$C]acetyltryptamine was measured.
Comparative Analysis of Assays The apparent specific activities measured with both methods were essentially identical (<20% difference). All assays were performed at least twice with duplicate measurements typically within 10%. Absorbance drift was minimal with fresh solution (presumably because of slow air oxidation) over the 20–30 min necessary for assay completion.

TABLE I

Apparent $K_{m(app)}$ and $k_{cat}$ values for acetyl transfer reactions catalyzed by GST-AANAT fusion and unmodified AANAT proteins. $K_{m(app)}$ values were measured according to "Materials and Methods" with a 1 mM (near saturating) concentration of the fixed substrate. The $k_{cat(app)}$ values shown are for the tryptamine reaction. The $k_{cat(app)}$ value for the serotonin reaction was measured to be 34 ± 2 $s^{-1}$. Values are displayed ± S.E.

| Enzyme form | Acetyl-CoA $K_{m(app)}$ | Tryptamine $K_{m(app)}$ | Serotonin $K_{m(app)}$ | $k_{cat(app)}$ |
|---|---|---|---|---|
| | mM | mM | mM | $s^{-1}$ |
| GST-AANAT | 0.289 ± 0.013 | 0.168 ± 0.014 | 0.241 ± 0.027 | 25 ± 1 |
| AANAT | 0.178 ± 0.013 | 0.125 ± 0.014 | | 25 ± 1 |

Kinetic Analysis $K_{m(app)}$ Measurements

Measurement of $K_{m(app)}$ for acetyl-CoA employed an acetyl-CoA concentration range of 0.1–2 mM (0.4 $K_m$–8 $K_m$) at fixed and near saturating tryptamine (1 mM). Measurement of $K_{m(app)}$ for tryptamine and serotonin employed a substrate concentration range of 0.5–1 mM (0.3 $K_m$–6 $K_m$) at fixed and near saturating acetyl-CoA (2 mM). Data were fitted to the equation $$v=V_m\cdot S/(K_m+S) \quad (Eq.\ 1)$$

using a nonlinear least squares approach (Macintosh computer program Kaleidograph™, Reading, Pa.), and the kinetic constants±S.E. errors are reported in Table I.
Two-Substrate Kinetic Measurements Two substrate kinetic analysis was performed with substrate concentrations given in FIG. 3, and the data were fitted to the sequential (ternary complex) mechanism equation (Equation 2) using the computer program Kinet-Asyst II™ (IntelliKinetics, State College, Pa.) based on the algorithms of Cleland (20), $$\upsilon = V_m \cdot A \cdot B / (K_a \cdot K_b \cdot K_{ma} \cdot B + K_{mb} \cdot A + A \cdot B) \quad \text{(Eq. 2)}$$

using a nonlinear least squares approach. Kinetic constants±S.E. are shown in Table II. $K_{ma}=K_m$ of acetyl-CoA in this work, $K_m$=dissociation constant for acetyl-CoA (dissociation constant to free enzyme where acetyl-CoA binds prior to tryptamine), $K_{mb}=K_m$ of tryptamine. Fitting to a ping-pong mechanism gave a significantly larger (5-fold) sum of squares of the residuals.

Kinetic Measurements with Inhibitors

Competitive inhibition kinetic analysis was done by fitting all of the data points to the linear competitive inhibition equation of KinetAsyst II™ based on the algorithms of Cleland (20), $$\upsilon = V_m \cdot S / K_m (1 + I/K_{is}) \quad \text{(Eq. 3)}$$

using a nonlinear least squares approach. The fixed substrate was assumed to be saturating. Kinetic constants±S.E. are shown in Table III.

Noncompetitive inhibition kinetic analysis was done by fitting all of the data points to the linear noncompetitive inhibition equation of KinetAsyst II™ based on the algorithms of Cleland (20), $$\upsilon = V_m \cdot S / [K_m (1 + I/K_{is}) + S(1 + I/K_{ii})] \quad \text{(Eq. 4)}$$

using a nonlinear least squares approach. Kinetic constants±S.E. are shown in Table III.

Uncompetitive inhibition kinetic analysis was done by fitting all of the data points to the linear uncompetitive inhibition equation of KinetAsyst II™ based on the algorithms of Cleland (20), $$V = V_m \cdot S / [K_m + S(1 + I/K_{ii})] \quad \text{(Eq. 5)}$$

using a nonlinear least squares approach. Kinetic constants±S.E. are shown in Table III.

The abbreviations are $K_{ii}=K_i$ intercept and $K_{is}=K_i$ slope based on double-reciprocal plot analysis according to the nomenclature of Cleland (21). The data for individual experiments with each inhibitor versus a varied substrate were fit to all three inhibitor models. Choice of kinetic fit was based on a combination of visual inspection and comparison of S.E. values and residuals for all three inhibition types

TABLE II

Steady state kinetics data from two-substrate kinetic assays with GST-AANAT.
See "Materials and Methods" and FIG. 3 for details. Values are given ± S.E. $K_{in}$ is the dissociation constant of the first binding substrate in an ordered sequential mechanism.

| Substrate | $K_m$ | $k_{cat}$ | $K_{in}$ |
|---|---|---|---|
|  | mM | s$^{-1}$ | mM |
| Tryptamine | 0.147 ± 0.023 | 30.4 ± 1.4 s$^{-1}$ |  |
| Acetyl-CoA | 0.212 ± 0.039 |  | 0.509 ± 0.156 | applied to the data sets (20). In the cases where uncompetitive inhibition was assigned, there were no significant improvements in the standard errors of sum of squares of the residuals (less than 2-fold) by including the extra inhibitory constant $K_{is}$. In the cases where competitive models were assigned, there were no significant improvements in the S.E. or the sum of squares of the residuals (less than 2-fold) by including the extra inhibitory constant $K_{ii}$. The lines drawn through the data points in the figures are derived from the fitted equations above.

RESULTS

Enzyme Production

Expression of the sheet GST-AANAT fusion plasmid in *E. coli* resulted in the production of active soluble GST-AANAT fusion protein (>5 mg/liter of culture). Purification using glutathione affinity chromatography afforded nearly homogeneously pure recombinant protein with the predicted molecular mass (approximately 50 kDa) as determined by SDS-polyacrylamide gel electrophoresis (see FIG. 2).

Figure 2:
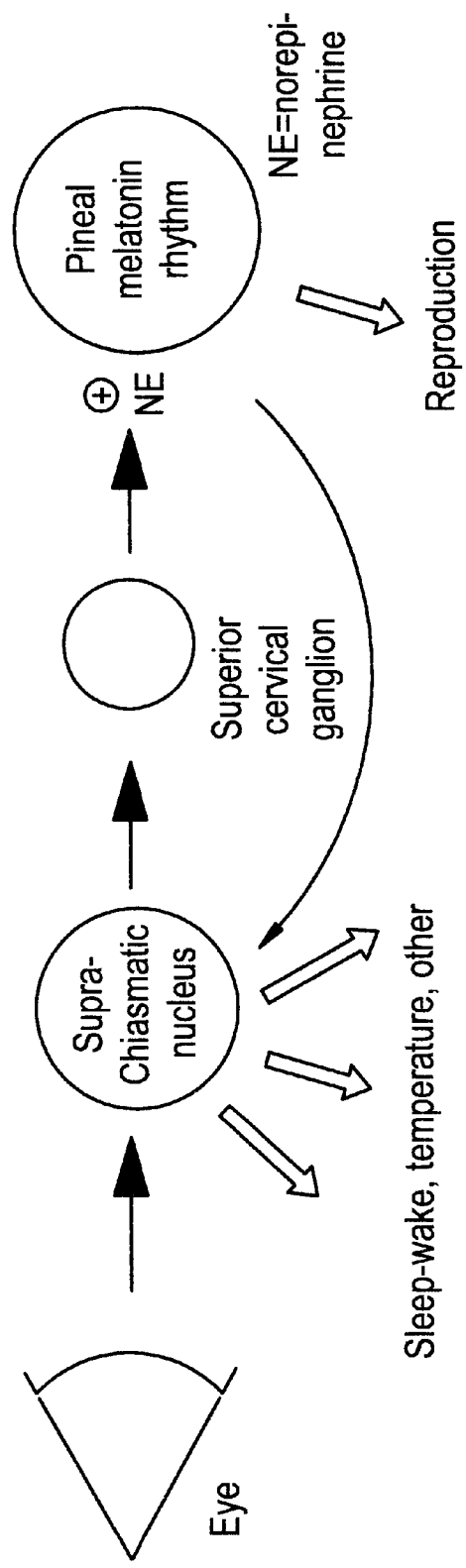
FIG. 2. Circadian Rhythm Controlled by SCN and Pineal

GST-free AANAT was obtained by thrombin cleavage of GST-AANAT (FIG. 2). The resulting product had kinetic characteristics essentially identical to those of GST-AANAT (Table I). GST-AANAT was used for further kinetic analysis because it was found to be more stable and easier to work with. The $k_{cat}$ of 25 s$^{-1}$ for a recombinant AANAT is similar to the reported $k_{cat}$ (80 s$^{-1}$) for a pure N-acetyl-CoA-dependent acetyltransferase (22). Furthermore, it was unlikely that the enzyme contained a large fraction of inactive material because preparations obtained using a variety of purification protocols had essentially identical turnover numbers.

Assay Development

Using the DTNB assay, GST-AANAT reactions display linear activity versus time for at least 3 min in the absence of reducing agents, and enzyme activity is linear with respect to enzyme concentration up to 500 nM. After background subtraction, interference from trace reducing agents from the enzyme preparations or the acetyl-CoA was shown to be inconsequential. There is insignificant CoASH formation in the absence of amine substrate in the enzyme range employed. As little as 1 nmol of product formation (3 μM) is detected reliably in a 0.3-ml reaction.

$K_m$ values for tryptamine and acetyl-CoA obtained with the DTNB assay showed good agreement with published values obtained with native sheet pineal AANAT[3] (3); specific activity values were approximately 1,000-fold higher for recombinant protein (3).

[3] When assayed at similar ionic strength (I~0.1), the $K_{m(app)}$ values for acetyl-CoA (0.1 mM) and tryptamine (0.1 mM) for GST-AANAT are nearly identical to the published data for native AANAT (see Ref. 3). These values are also in a convenient range to perform kinetic mechanism studies as outlined below. The $k_{cat(app)}$ and $K_{m(app)}$ generated with serotonin were nearly indistinguishable from those obtained with tryptamine (see Table I).

Two-Substrate Kinetics $K_m$ values were obtained for tryptamine using a range of acetyl-CoA concentration. A double-reciprocal analysis of these data formed an intersecting line pattern (FIG. 3) that is characteristic of a ternary complex (sequential) mechanism. In contrast, a ping-pong mechanism (see FIG. 5) is typically characterized by a parallel line pattern (21).

TABLE III

Figure 5:
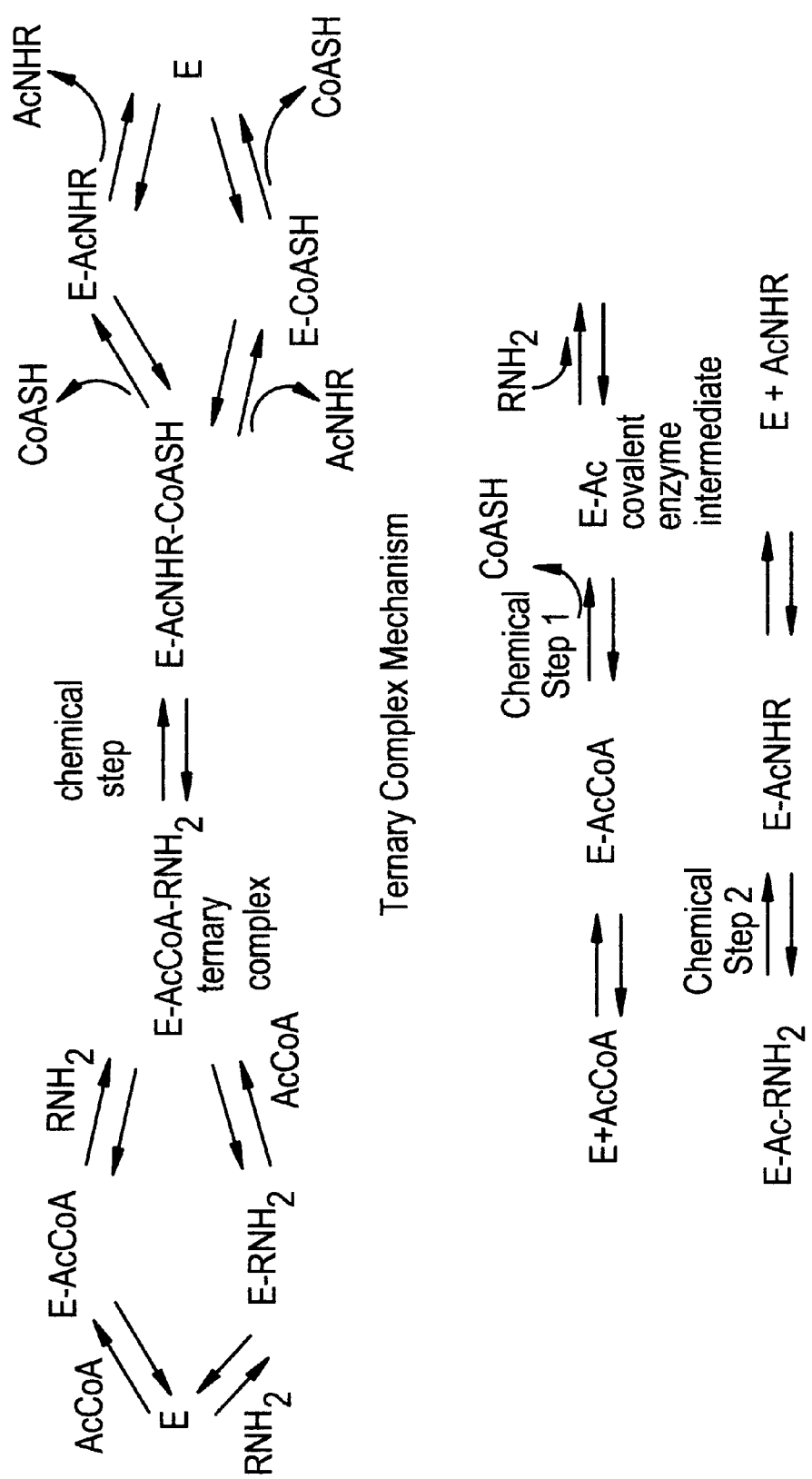
FIG. 5. Two Major Alternative Kinetic Schemes for Acetyltrasferase
Figure 6:
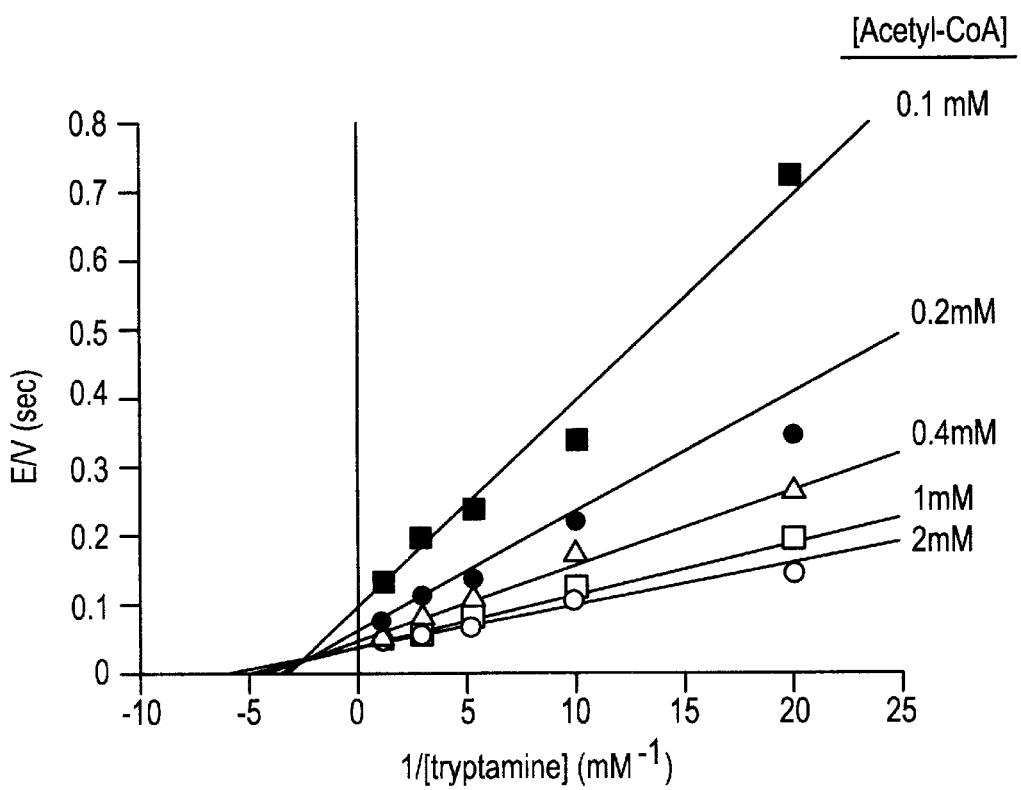
FIG. 6. I/V vs. 1/Tryptamine at Different Acetyl-CoA Concentration
Figure 7:
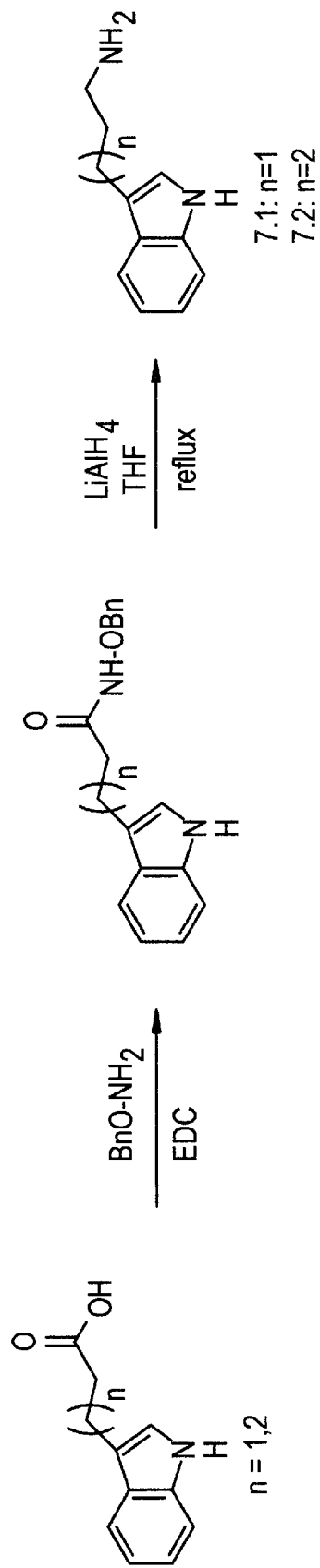
FIG. 7. Synthesis of Homologated Tryptamines

Inhibitor data with GST-AANAT
See "Materials and Methods" and FIGS. 5–7 for further details. Values are shown ± S.E. 20

| Inhibitor | Varied substrate | Constant substrate | Inhibitor pattern | $K_{is}$ | $K_{si}$ |
|---|---|---|---|---|---|
| | | | | mM | mM |
| Desulfo-CoA | Acetyl-CoA | Tryptamine (1 mM) | Competitive | 1.02 ± 0.20 | |
| | Tryptamine | Acetyl-CoA (0.2 mM) | Noncompetitive | 1.34 ± 0.45 | 1.49 ± 0.23 |
| Tryptophol | Tryptamine | Acetyl-CoA (1 mM) | Competitive | 0.680 ± 0.078 | |
| | Acetyl-CoA | Tryptamine (0.2 mM) | Uncompetitive | | 1.36 ± 0.12 |
| N-Acetyltryptamine | Tryptamine | Acetyl-CoA (1 mM) | Noncompetitive | 0.205 ± 0.029 | 0.916 ± 0.160 |
| | Acetyl-CoA | Tryptamine (0.2 mM) | Uncompetitive | | 0.331 ± 0.023 |

Desulfo-CoA as a Dead End Analog Inhibitor

Figure 4:
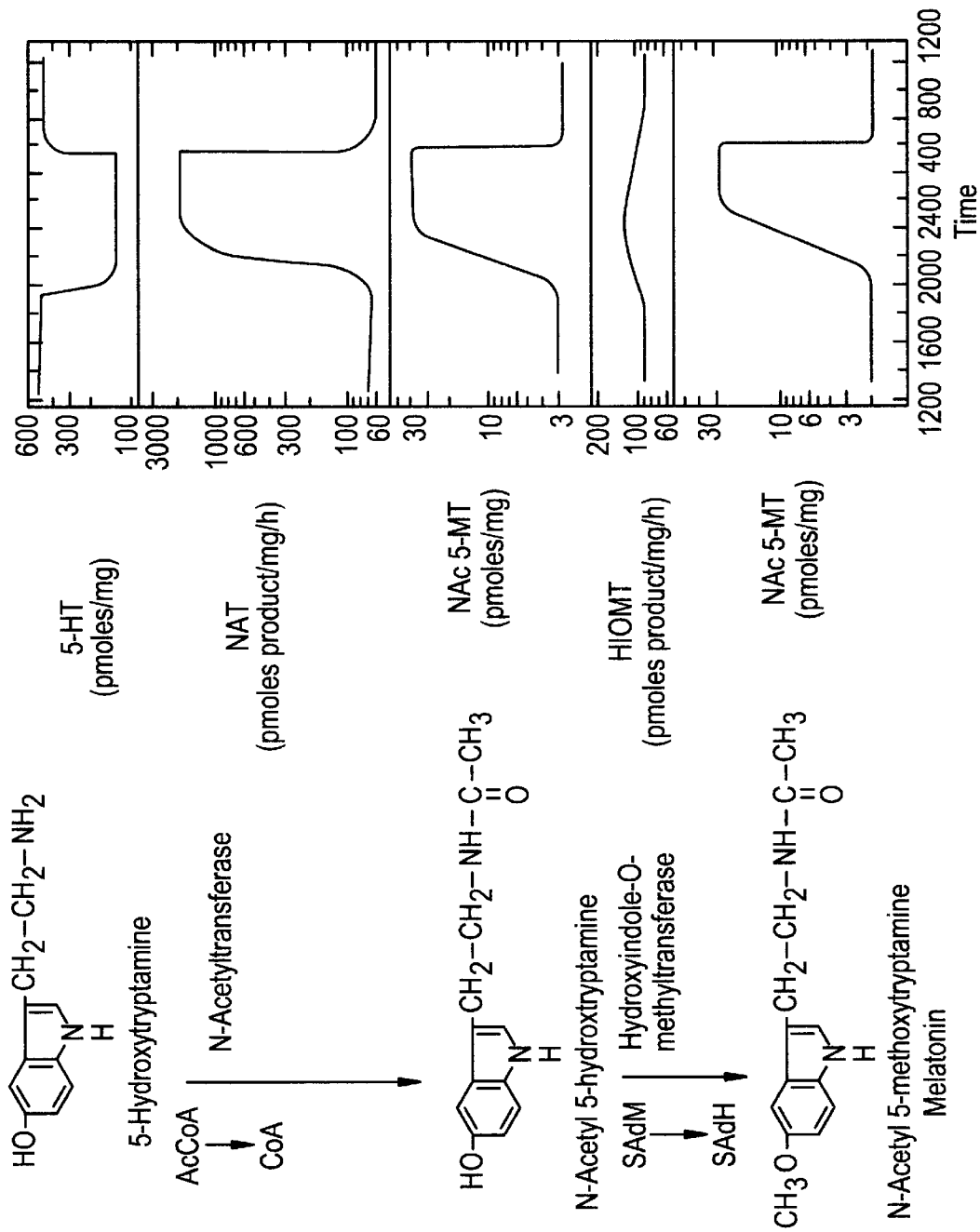
FIG. 4. Day/Night Rhythm of Pineal Hormones and Enzymes

Dead end analog inhibitors are compounds that resemble one substrate or the other but are unable to serve as substrates because of structural differences. Desulfo-CoA lacks the terminal sulfur atom of CoASH (FIG. 4) and is a potential dead end inhibitor of AANAT. It was found to be a linear competitive inhibitor versus acetyl-Co-A at saturating tryptamine concentration with a $K_{is}$ of 1 mM, only 2-fold larger than the dissociation constant of acetyl-CoA (0.51 mM) (FIG. 5). Desulfo-CoA was also tested as a GST-AANAT inhibitor at fixed acetyl-CoA concentration and varying concentrations of tryptamine (FIG. 5). It was found to be noncompetitive versus tryptamine as opposed to uncompetitive, the latter being the expected pattern if tryptamine binds first in an ordered ternary complex mechanism (21).

Tryptophol as a Dead End Analog Inhibitor

The structural analog to tryptamine in which the primary amine function is replaced by a hydroxyl function (tryptophol) (see FIG. 4) could theoretically be an alternative AANAT substrate. To investigate this possibility, 1 mM tryptophol was incubated with 500 mM GST-AANAT in the presence of 1 mM acetyl-CoA for up to 3 min. Under these conditions no detectable transfer took place, indicating that tryptophol is acetylated at least 400-fold less efficiently by GST-AANAT compared with tryptamine.

Because tryptophol was not a substrate, it was evaluated as a potential GST-AANAT inhibitor. As expected, tryptophol was a linear competitive inhibitor of tryptamine (Table III). In studies with tryptophol as the inhibitor and acetyl-CoA as the varied substrate, at subsaturating concentration of tryptamine there was a clear uncompetitive pattern of inhibitors as reflected in the parallel line pattern of FIG. 6. This pattern indicates that acetyl-CoA must bind earlier than tryptophol for tryptophol inhibition to take place.

N-Acetyltryptamine is a Product Inhibitor

N-Acetyltryptamine is one of the two products of the N-acetyltransferase reaction (see FIG. 1), and its inhibitory behavior was evaluated with GST-AANAT because reaction products can be useful diagnostic tools for kinetic mechanism studies. N-Acetyltryptamine was found to be a clear noncompetitive inhibitor versus tryptamine as the varied substrate (FIG. 7 and Table III). N-Acetyltryptamine was found to be an uncompetitive inhibitor versus acetyl-CoA at fixed, subsaturating tryptamine concentration (tryptamine concentration≈$K_m$ of tryptamine, Table III).

DISCUSSION

DTNA-based AANAT Assay

Previously published kinetic assays for AANAT have relied on radioactive incorporation of acetyl ($^3$H or $^{14}$C) into the acetylated product (3, 12, 23) or high pressure liquid chromatographic analysis (24, 25). These assays were developed for high sensitivity as required for detection of enzyme activity in small biological samples. However, they require complex extraction procedures and are not practical for routine analysis of large numbers of samples as required for detailed mechanistic studies or inhibitor screens. The less complicated DTNB assay described in this report meets this requirement.

The potential difficulty with this approach was that reducing agents such as dithiothreitol and β-mercaptoethanol react with DTNB (Ellman's reagent). Indeed, GST-AANAT is somewhat unstable in the absence of reducing agents, losing greater than 50% activity within 2 h at 4° C. (data not shown). However, the enzyme was stable within the short incubation periods used in these studies (less than 3 min). It was shown unequivocally that CoASH generation was coupled tightly to N-acetyltryptamine formation, and the activity was linear with time and enzyme concentration. An attractive feature of the DTNB detection assay is that it allows any potential amine substrate to be tested easily, providing it does not react with DTNB. Of note, a continuous spectrophotometric assay with DTNB was not possible because DTNB inhibited GST-AANAT activity.

Kinetic Mechanism of GST-AANAT

A generally useful approach to kinetic analysis of two-substrate enzymes is one in which both substrates are varied within the same experiment. It is well accepted that a double-reciprocal plot that results in intersecting lines suggests a ternary complex mechanism and that a parallel line pattern is characteristic of a ping-pong mechanism (21). Previous experiments using this approach to analyze crude preparations on AANAT from rat and bird pineal glands suggest that different mechanisms were involved (23, 26). This difference is inconsistent with the high homology among vertebrate AANATs, especially within the putative binding domains and the putative catalytic site (4, 10). The reported differences in the apparent mechanism of catalysis may reflect contaminants in the partially purified preparations as the assays appeared to be performed under similar conditions of pH and ionic strength. The potential problem with contaminants is avoided by the use of purified expressed GST-AANAT as described in this report.

The most important advance in this study was the evidence that a ternary complex mechanism is involved, as indicated by the clear intersecting line pattern. It should be noted that although this analytical approach has correctly predicted the mechanistic behavior of the best characterized acetyltransferases (15, 27, 28) it is not impossible that a covalent enzyme intermediate occurs. However, if a covalent enzyme intermediate occurs, it must form after both substrates are bound and decompose before either product leaves.

The next issue addressed was the order of binding of substrates which precedes ternary complex formation. Three major schemes are possible (i) ordered with acetyl-CoA binding first; (ii) ordered with tryptamine binding first; and (iii) random substrate binding. To discriminate among these possibilities dead end inhibitors were used (21).

Desulfo-CoA dead end analog of acetyl-Co-A (see FIG. 4), was shown to be a linear competitive inhibitor with respect to acetyl-CoA and a noncompetitive inhibitor with respect to tryptamine. These results rule out an ordered mechanism where tryptamine binds before acetyl-CoA. In such a mechanism, desulfo-CoA would have been uncompetitive with respect to tryptamine. The desulfo-CoA experiments leave open the possibilities that there is random binding of acetyl-CoA and tryptamine or ordered binding of acetyl-CoA before tryptamine. Another interesting point is the apparent similarity in affinity which GST-AANAT displays toward acetyl-CoA ($K_d$=0.51 mM) and desulfo-CoA ($K_1$=1 mM). It suggests that the thioester function contributes little binding energy in the ground state complex.

Tryptophol (FIG. 4) was next evaluated as a GST-AANAT substrate/inhibitor. It was shown that replacement of the amino function of tryptamine with a hydroxy group prevents enzyme-catalyzed acetyl transfer. The lack of reactivity suggests that the nucleophilicity of the amine is critical for enzyme-catalyzed reaction because tryptophol can bind with reasonable affinity to AANAT as demonstrated by its inhibitory behavior (see below). Interestingly, the O-acetyltransferase carnitine acetyltransferase is able to process the amino-substrate at a $k_{cat}$ only 13-fold lower than the normal hydroxy substrate (29). This altered reactivity between the two enzymes suggests that there may be a mechanistic difference in the chemical steps catalyzed between these two classes of acetyltransferases (O and N). Tetrahydrodipicolinate N-succinyltransferase also shows no reactivity toward the corresponding oxygen analog (30).

Figure 3:
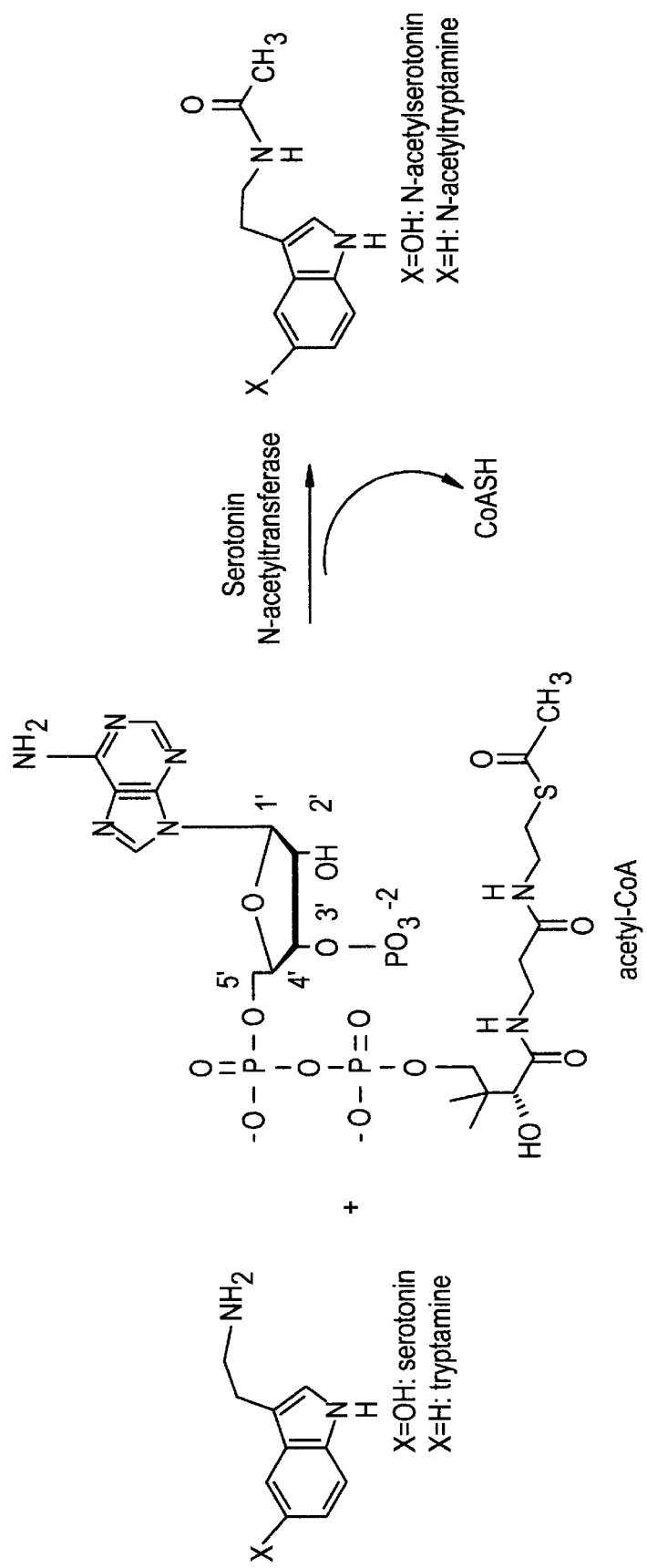
FIG. 3. Serotonin N-acetyltrasferase (AANAT) Reaction

As expected, tryptophol proved to be a linear competitive inhibitor of GST-AANAT versus the varied substrate tryptamine. It was a clear uncompetitive inhibitor versus acetyl-CoA. Fitting the data to a noncompetitive fit gave no significant lessening of the residuals and gave a $K_{is}$ that was more than 10 times higher than the $K_{ii}$ with a very large error (≈100%). These results strongly suggest that acetyl-CoA must bind before tryptamine to the enzyme, i.e. that there is an ordered mechanism. Although this inhibitory pattern is compatible with a ping-pong kinetic mechanism, a ping-pong mechanism is ruled out by the intersecting line pattern in the two substrate kinetic analysis (FIG. 3). The ordered binding suggests either (i) a conformational change in the protein which causes the tryptamine binding pocket to become accessible only after acetyl-CoA binds or (ii) tryptamine undergoes an important, direct noncovalent binding interaction with acetyl-CoA in the enzyme active site. Differentiation between these possibilities awaits further structural studies.

CoASH was not evaluated as a reversible inhibitor in the spectrophotometric assay because it reacts with DTNB. It also forms $(CoAS)_2$ in the absence of reducing agents, and the use of reducing agents in the radiochemical assay would require extensive kinetic characterization of the enzyme in the presence of such reagents, which is beyond the scope of this investigation. The reaction product N-acetyltryptamine is a noncompetitive inhibitor versus tryptamine and an uncompetitive inhibitor versus acetyl-CoA. This strongly suggests that AANAT obeys an ordered BiBi ternary complex mechanism with N-acetyltryptamine being the first product released followed by CoASH. The noncompetitive inhibition pattern versus tryptamine likely is caused by the binding of N-acetyltryptamine to both the acetyl-CoA-bound GST-AANAT form as well as the CoASH-bound GST-AANAT form. The lack of a slope effect in the inhibition of N-acetyltryptamine versus acetyl-CoA (at subsaturating tryptamine) presumably stems from the fact that the chemical step is very weakly reversible since a thioester bond ($\Delta G_{hydrolysis}$ of acetyl-CoA=−7.5 kcal/mol) is exchanged for an amide bond ($\Delta G_{hydrolysis}$ of propionamide=−2.1 kcal/mol) (21, 31).

REFERENCES

1. Klein, D. C., and Weller, J. L. (1970) *Science* 169, 1093–1095.
2. Arendt, J. (1995) *Melctonin and the Mammalian Pineal Gland*, Chapman and Hall, London.
3. Voisin, P., Namboodiri, M. A. A., and Klein, D. C. (1984) *J. Biol. Chem.* 259, 10913–10918.
4. Klein, D. C., Roseboom, P. H., and Coon, S, L. (1996) *Trends Endocrinol. Metab.* 7, 106–112.
5. Coon, S. L., Roseboom, P. H., Baler, R., Weller, J. L., Namboodiri, M. A. A., Koonin, E. V., and Klein, D. C., (1995) *Science* 270, 1681–1683.
6. Borjigin, J., Wang, M. M., and Snyder, S. H. (1995) *Nature* 378, 783–785.
7. Coon, S. L., Mazuruk, K., Bernard, M., Roseboom, P. H., Klein, D. C., and Rodriguez, I. R. (1996) *Genomics* 34, 76–84.
8. Bernard, M., Iuvone, P. M., Cassone, V. M., Roseboom, P. H., Coon, S. L., and Klein, D. C. (1997) *J. Neurochem.* 68, 213–224.
9. Roseboom, P. H., Coon S. L., Baler, R., McCune, S. K., Weller, J. L., and Klein, D. C. (1996) *Endocrinology* 137,3033–3045.
10. Klein, D. C., Coon, S. L., Roseboom, P. H., Weller, J. L., Bernard, M., Gastel, J. A., Zatz, M., Iuvone, P. M., Rodriquez, I. R., Begay, V., Falcon, J., Cahill, G. M., Cassone, V. M., and Baler, R. (1997) *Recent Progr. Horm. Res.* 52, 307–357.
11. Vatsis, K. P., Weber, W. W., Bell, D. A., Dupret, J. M., Evans, D. A., Grant, D. M., Hein, D. W., Lin, H. J., Meyer, U. A. Relling, M. V., et al. (1995) *Pharmacogenetics* 5, 1–17.
12. Deguchi, T. (1975) *J. Neurochem.* 24, 1083–1085.
13. Sim, E., Hickman, D., Coroneos, E., and Kelly, S. L. (1992) *Biochem. Soc. Trans.* 20, 304–309.
14. Weber, W. W., and Cohen, S. N. (1967) *Mol. Pharmacol.* 3, 266–273.
15. Jencks, W. P., Gresser, M. Valenzuela, M. S., and Huneeus, F. C. (1972) *J. Biol. Chem.* 247, 3756–3760.
16. Riddle, B., and Jencks, W. P. (1971) *J. Biol. Chem.* 246, 3250–3258.
17. Cheon, H. -G., and Hanna, P. E. (1992) *Biochem. Pharmacol.* 43, 2255–2268.
18. Dupret, J. -M., and Grant, D. M. (1992) *J. Biol. Chem.* 267, 7381–7385.
19. Riddles, P. W., Blakeley, R. L., and Zerner, B. (1993) *Methods Enzymol.* 91, 49–60.
20. Cleland, W. W. (1979) *Methods Enzymol.* 63, 103–138.
21. Segel, I. H. (1975) *Enzyme Kinetics: Behavior and Analysis of Rapid Equilibrium and Steady-state Enzyme Systems*, Wiley-Interscience, New York.
22. Gehring, A. M., Lees, W. J., Minidiola, D. J., Walsh, C. T., and Brown, E. D. (1996) *Biochemistry* 35, 579–585.
23. Wolfe, M. S., Lee, N. R., and Zatz, M. (1995) *Brain Res.* 669, 100–106.
24. Thomas, K. B., Zawilska, J., and Iuvone, P. M. (1990) *Anal. Biochem.* 184, 228–234.
25. Fajardo, N., Abrue, P., and Alonso, R. (1992) *J. Pineal Res.* 13, 80–84.

26. Morrissey, J. J., Edwards, S. B., and Lovenberg, W. (1977) *Biochem. Biophys, Res. Commun.* 77, 118–123.
27. Shaw, W. V., and Leslie, A. G. W. (1991) *Annu. Rev. Biophys. Biophys. Chem.* 20, 363–386.
28. Colucci, W. J., and Grandour, R. D. (1988) *Biorg. Chem.* 16, 307–334.
29. Jenkins, D. L., and Griffith, O. W. (1985) *J. Biol. Chem.* 260, 14748–14755.
30. Berges, D. A., DeWolf, W. E., Dunn, G. L., Newman, D. J., Schmidt, S. J., Taggart, J. J., and Gilvarg, C. (1996) *J. Biol. Chem.* 261, 6160–6167.
31. Sober, H. A. (ed) (1970) *Handbook of Biochemistry: Selected Data for Molecular Biology*, 2nd Ed., p. J-184, CRC Press, Cleveland.
32. Yang, X. -J., Ogryzko, V. V., Nishikawa, J., Howard, B. H., and Nakatani, Y. (1996) *Nature* 382, 319–324.

EXAMPLE 2

1) Protein Expression and Purification

Expression of eukaryotic proteins in bacteria is unpredictable. Indeed, efforts to express the rat and human AANAT protein in *E. coli* have so far been unsuccessful. In contrast, the sheep enzyme which is 80% identical at the amino acid level to rat and human can be expressed in *E. coli* as a soluble protein (51). GST-AANAT can be obtained in approximately 90% purity with a yield of 5–10 mg/L of *E. coli* culture after purification with glutathione-agarose. Optimization of conditions for production of this fusion protein has led to the induction being carried out at 22–24° C. for 5–6 h after 0.2 mM IPTG to prevent inclusion body formation. The fusion protein can be concentrated to>6 mg/mL using an Amicon filter and appears to be stable for at least 6 months when stored at −80° C. in the presence of a thiol-reducing agent. Activity assay with tryptamine as the amine substrate and acetyl-CoA showed that the GST-AANAT fusion protein is highly active (with a specific activity about 1000-fold times the partially purified enzyme derived from pineal gland). The enzymatic reaction displayed Michaelis-Menten behavior and showed $K_m$'s very similar (within 2-fold) to the pineal-derived material (51). Specific activity is also highly reproducible from batch to batch. Cleavage of the fusion protein with thrombin followed by repeat glutathione-affinity chromatography has afforded GST-free AANAT. GST-free AANAT has behaved nearly identically in enzyme assays in terms of $k_{cat}$ and $K_m$'s and so for much of the enzymology discussed below the GST-AANAT fusion protein which is easier to obtain and more stable has been employed (51).

Spectrophotometric Assay Development

The enzymatic assays available for AANAT were direct, radioactive assays. [$^3$H]- or [$^{14}$C]-labelled acetyl-CoA commonly used and the acetylated product is separated either chromatographically or by selective extraction into organic solvent (41, 52). While this assay has proved useful because of its high sensitivity in measuring activity in crude cell extracts, it is cumbersome for mechanistic studies. Thus indirect methods to measure CoASH formation were tested.

After several attempts at direct assays and enzyme-coupled assays, the most successful approach proved to be quantitating CoASH formation of the quenched mixture with Ellman's reagent (5,5'-dithiobis-(2-nitrobenzoic acid; DTNB). Because the enzyme proved unstable in the absence of thiol reducing reagents, continuous assay in the presence of DTNB was not possible. However, by running the reaction in the presence of very low levels of reducing reagent (1–10 mM DTT) for short periods of time (up to 3 min), kinetic behavior is excellent. The enzyme activity is linear with respect to time and enzyme concentration under initial conditions (51). Quantitatively, the specific activity is essentially identical to the conventional radioactive assay. Importantly, there is no evidence of significant uncoupling of CoASH production and amide formation with any substrates (or non-substrates) tested.

Steady-State Kinetic Mechanism

Acetyltransferase enzymes appear to use one of two major mechanistic pathways (FIG. 5). The first involves a ternary complex mechanism where both substrates bind to the active site concurrently and the chemical step involves direct transfer of the acetyl group from acetyl-CoA to the amine substrate. Enzymes following ternary complex pathways include chloramphenicol acetyltransferase (53) and carnitine acetyltransferase (54). The second major class of kinetic schemes are ping-pong mechanisms where acetyl-CoA binds first and reacts with an enzyme-nucleophile creating an acetylated-enzyme intermediate and CoASH is released. In the second step, the amine substrate binds and reacts with the acetylated enzyme to produce the N-acetylamine product. Well-studied acetyltransferases that follow ping-pong mechanisms are arylamine acetyltransferase (55) and choline acetyltransferase (56, 57). A standard method to distinguish among these possibilities is to carry out a steady-state kinetic analysis where both substrate concentrations are varied within the same experiment. Ternary complex mechanisms usually show an intersecting line pattern whereas ping-pong mechanisms usually show a parallel line pattern. Previously reported conflicting models for crude AANAT from pineal cell extracts support alternative mechanisms (58, 59). Using the purified recombinant sheet AANAT enzyme and the spectrophotometric assay, a clear intersecting line pattern was observed, supporting a ternary complex mechanism (51, 60).

In studies with dead-end inhibitor analogs: tryptophol, desulfo-CoA and the product N-acetyltryptamine, further details of the proposed ternary complex mechanism were deduced. Overall, the inhibitory patterns observed in these experiments support an "ordered BiBi" ternary complex mechanism where acetyl-CoA binds to the enzyme prior to tryptamine and then the products N-acetyltryptamine and CoASH are successively released (51). This type of mechanism suggests synergistic binding between the CoA and the substrate. A significant possibility is that the binding of CoA results in an enzyme conformational change which encourages the binding of tryptamine (or serotonin).

Amine Analogs as Probes of Active Site Structure and Catalytic Mechanism

The effects of alkyl chain extension, alkyl branching, halogen substitution, microviscosity effects, and transition state analog inhibitors were investigated. Although several amine analogs have been shown to be AANAT substrates using the pineal-derived enzyme (41), little is known about the potential for tryptamine analogs with variations on the amino-ethyl side chain to be tolerated as alternative substrates for AANAT. (FIG. 6).

Chain Extension

The first objective of these studies was to determine the tolerance of alkyl chain length for substrate processing efficiency. While it has been previously shown that several arylethylamine analogs are AANAT substrates, derivatives with propylamine and butylamine chains have never been tested. indole-propylamine (7.1) and indole-butylamine (7.2) analogs (FIG. 7) as AANAT substrates or inhibitors. If these compounds were in fact AANAT substrates, it would create the possibility of designing inhibitors with a much wider array of substitutions. In the natural substrate serotonin (or tryptamine), the alkyl side chain are not readily substituted with leaving groups. Thus a- and b-halo substituted tryptamines would be highly unstable, difficult to make and impractical to use. In contrast, the corresponding b-substituted compounds in the series (7,1) and (7.2) would be much more synthetically accessible and stable, not subject to the "benzylic effect." (ref.). Indole-propylamine (7.1) and indole-butylamines (7.2) are not commercially available and were prepared as shown (FIG. 7) (6l). Thus the commercially available carboxylic acid derivatives were converted to the O-benzyl-hydroxamic acid derivatives and these were exhaustively reduced with $LiAlH_4$ to produce the amines which were stored as the hydrochloride derivatives. Enzymatic evaluation of these amines using the spectophotometric assay revealed that both were substrates with kinetic constants shown in Table 3. While the optimum chain length is 2-carbons as present in the natural substrate serotonin rather than 3- or 4-carbons as in compounds 7.1 and 7.2, AANAT shows significant tolerance for chain extension. Thus b-substituted analogs of 7.1 could be effective tools for mechanistic studies or inhibitors.

Table 1

Steady-State Kinetic Parameters for Tryptamine Analogs with AANAT

| tryptamine analog | $K_m$ (mM) | $k_{cat}$ (s$^{-1}$) | $K_i$ (mM) | other |
|---|---|---|---|---|
| serotonin | 0.24 ± 0.03 | 34 ± 1 s$^{-1}$ | | |
| tryptamine | 0.17 ± 0.01 | 25 ± 1 s-1 | | |
| 7.1 | 0.77 ± 0.07 | 5.5 ± 0.2 | — | |
| 7.2 | 1.7 ± 0.1 | 4.2 ± 0.1 | — | |
| (+/−) a-methyltryptamine | 2.7 ± 0.2 | 16 ± 0.4 | — | 9:1 preference for R-isomer vs. S-isomer as substrate |
| Nw-methyltryptamine | 3.8 ± 0.7 | 2.0 ± 0.1 | — | chemical step is rate-determining (viscosity studies) |
| (+/−) a-trifluoromethyltryptamine | — | — | 3 ± 1 | |

Methyl-substituted Analogs

Figure 8:
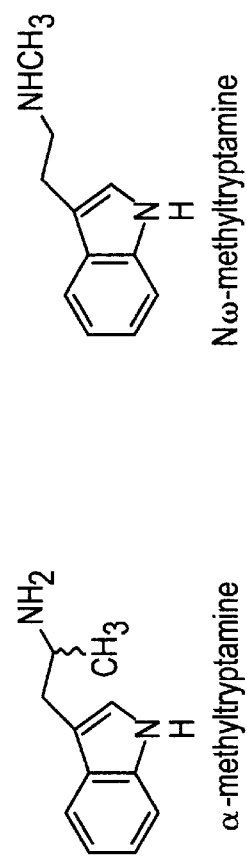
FIG. 8. Methyltryptamine Analogs

Another important selectivity issue was addressing the effects of a-methyl and Nw-methyl-substitutions of tryptamine analogs (FIG. 8) on AANAT catalysis. These compounds would assess the active site tolerance to a-branching and the steric hindrance associated with converting the nucleophilic primary amine to a secondary amine. These compounds were obtained from commercial sources and tested as AANAT substrates. Both a-methyltryptamine (racemic) and Nw-methyltryptamine were AANAT substrates although again with significantly reduced $k_{cat}$ and $K_m$ compared to tryptamine (Table 3). Using these compounds. Reaction of (±) a-methyltryptamine with acetyl-CoA catalyzed by AANAT was allowed to proceed to 50% completion. Isolation of the recovered starting material and the acetylated product by extraction and chromatography afforded milligram quantities of each. Optical rotations of the starting material and product were obtained and by comparison to reported values for the former (62), demonstrated that AANAT selectively processed (9:1) the R-isomer of a methyltryptamine vs. the S-isomer. Knowledge of this stereoselective preference will be useful for designing the most effective inhibitors.

a-Trifluoromethyltryptamine

Figure 9:
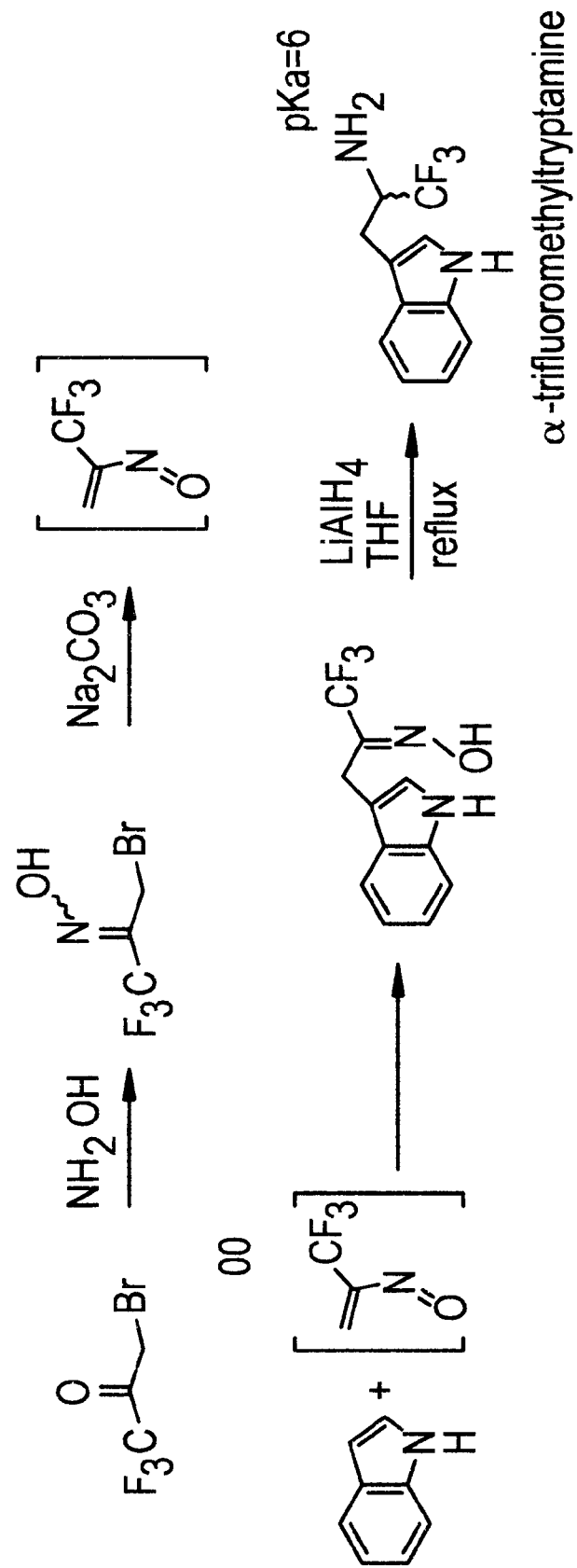
FIG. 9. Synthesis of α-trifluoromethyltryptamine

Information about electronic requirements of the tryptamine substrate is important in understanding catalysis and potentially of great use for inhibitor design. Lowering the amine $pK_a$ by electronegative atom substitution nearby would result in a larger concentration of the neutral amine at pH 7. Depending on the mechanism of AANAT this could lead to a substrate with a reduced $K_m$ or it could lead to an inhibitor since a neutral amine with a reduced $pK_a$ is generally less nucleophilic than a neutral amine with a higher $pK_a$. Since the atomic radius of fluorine is only 0.2 Å greater than hydrogen, fluorine is close to isosteric with hydrogen but can significantly change electronic properties because of its extreme electronegativity. Fluorine-substitution has been a powerful way to probe enzyme mechanism and generate inhibitors (63). Trifluoromethyltryptamine was synthesized as shown in FIG. 9 (64).

Commercially available bromotrifluoromethyl ketone was converted to the oxime by reaction with hydroxylamine. The oxime was used to generate the vinyl nitroso derivative which was used in situ to react in a 4+2 cycloaddition and produce the 3-substituted indole. Reduction of this material with $LiAlH_4$ led to generation of racemic a-trifluoromethyltryptamine. a-Trifluoromethyltryptamine was calculated to have a primary amine $pK_a$ of approximately 6. In contrast to the isosteric a-methyltryptamine, a-trifluoromethyltryptamine was not detectably an AANAT substrate. It was thus tested as a potential competitive inhibitor and was found to be a modest inhibitor with $K_i^a$ 3 mM, similar to the $K_m$ of a-methyltryptamine (see Table 1). This suggests that a-trifluoromethyltryptamine can bind about as well as a-methyltryptamine to AANAT but may lack the nucleophilicity to undergo reaction. It is not clear from these studies if the lack of tight binding of a-trifluoromethyltryptamine represents steric or electronic repulsion of the fluorines offset by the tighter binding of the neutral amine function, or if a positively charged amine is the preferred state for binding to AANAT (65).

Viscosity studies

An important part of enzyme mechanistic analysis is to determine which step(s) is (are) rate-determining for the enzyme reaction. After the binding of the substrates to the enzyme, there are several potential rate-determining steps, the chemical step or one of the product release steps. Since stead-state analysis revealed an ordered BiBi ternary complex kinetic mechanism with CoASH as the final product released, if viscosity studies showed that product release were rate-determining then CoASH release would likely be the slow step.

Viscosity effects can be useful for distinguishing product release steps from non-diffusional steps (66). The principle of using viscosity effects to study enzyme reaction kinetics is based on the fundamental inverse relationship between microviscosity and diffusional rates. Thus a linear increase in microviscosity caused by a microviscogen such as sucrose causes a linear decrease in the diffusion of small molecules. Since little diffusion is involved in the chemical step, this step is taken as viscosity-insensitive. However, viscogenic agents (which are used at rather high concentrations) can cause non-diffusion related effects by interacting with the enzyme or substrate. Controls for these non-diffusional effects must be carried out. One of the best controls is to measure the effects of the viscogen on the enzymatic reactions of "poor substrates" (66). Since poor substrates in general would be expected to have reduced $k_{cat}$ values because the rate of their chemical steps are reduced, any viscosity effects observed would be expected to be related to non-diffusional or "artifactual" effects. As mentioned above Nw-methyltryptamine shows a substantially reduced $k_{cat}$ compared to tryptamine and thus should serve as a "poor substrate".

Figure 10:
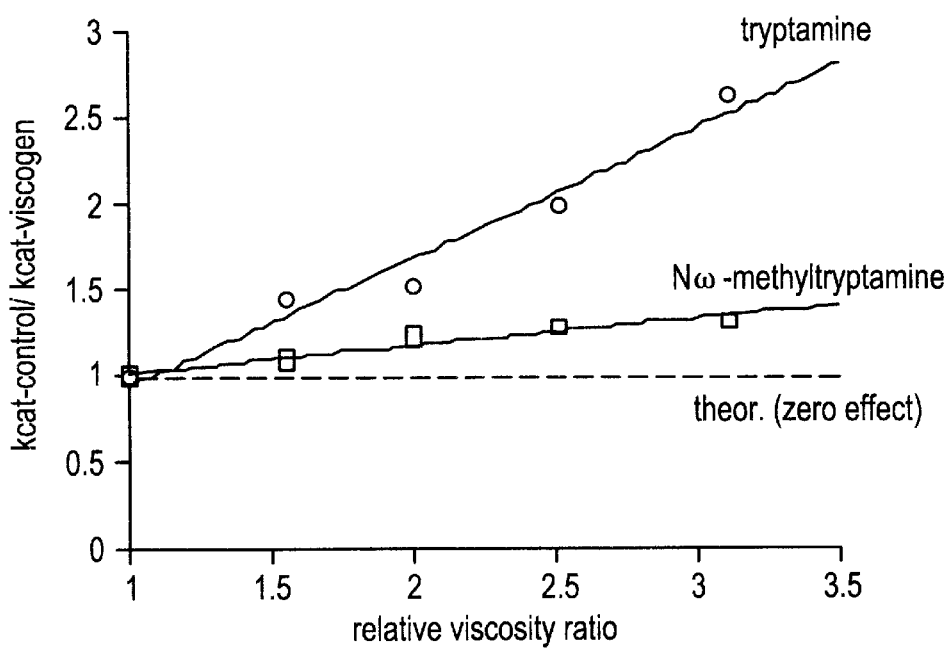
FIG. 10. Kcat-kcontrol/kcat-viscogen v. Relative Viscosity for AANAT

In the experiment with sucrose as the microviscogen, small effects on plots of $K_{control}/k_{viscogen}$ vs. relative viscosity [$k_{cat}$ (slope=+0.16±0.03)(FIG. 10) and $k_{cat}/K_m$ (slope=−0.14±0.03) (not shown)] were observed. The theoretical slope values are zero for poor substrates so the experimental values are close to ideal suggesting that non-specific, artifactual effects are small for the AANAT reaction. For, the standard substrate tryptamine the $k_{cat}$ effect (slope=+0.75±0.08) was substantial (FIG. 10) and close to the theoretical slope of 1 for a completely diffusion-limited reaction (66). Taken together, these results suggest that for the poor substrate, the chemical step is rate-determining but that for a more natural substrate like tryptamine, product release (or a conformational change associated with product release) is largely rate-determining.

Synthesis of bisubstrate analog 11.1

Figure 11:
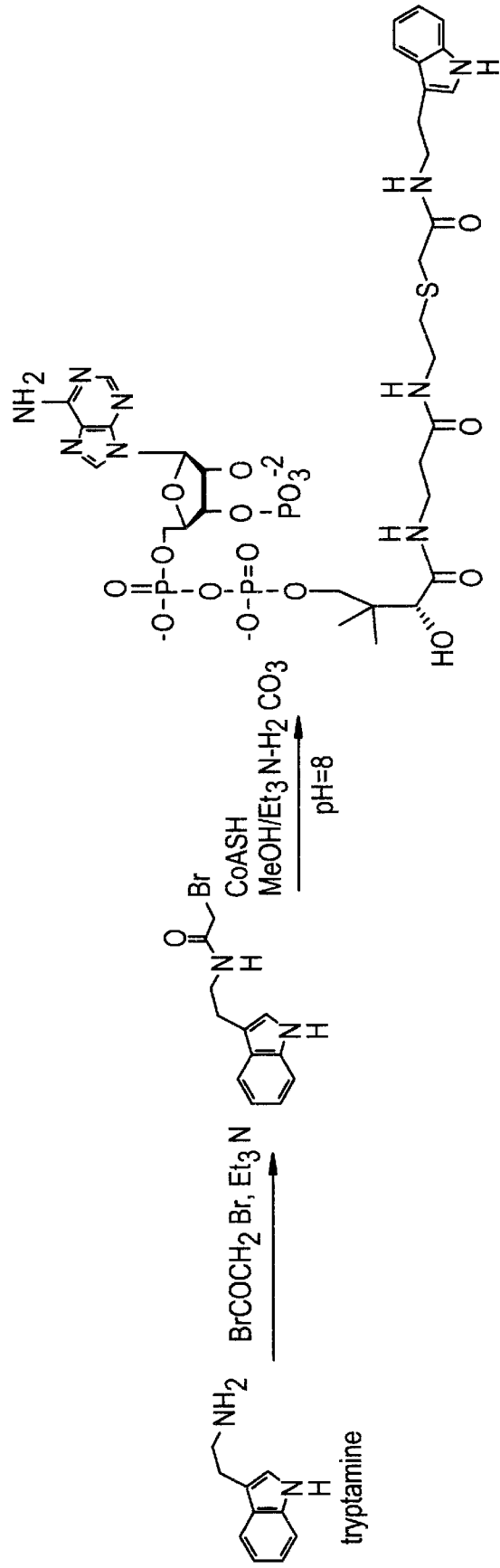
FIG. 11. Synthesis of Bisubstrate Analog 11.1

Tryptamine was reacted with commercially available bromacetyl bromide and the bromacetamide was isolated and characterized (FIG. 11). The bromacetamide was reacted with CoASH in mildly basic aqueous solution. After no free thiol could be detected by DTNB assay, the crude reaction mixture was purified by extraction and reverse phase HPLC to yield pure 11.1 (50%) yield). Structure and purity of 11.1 was ascertained by $^{31}P$ NMR, $^1H$ NMR, electrospray MS, UV, and HPLC.

Evaluation of 11.1 as an Inhibitor of AANAT

Figure 12:
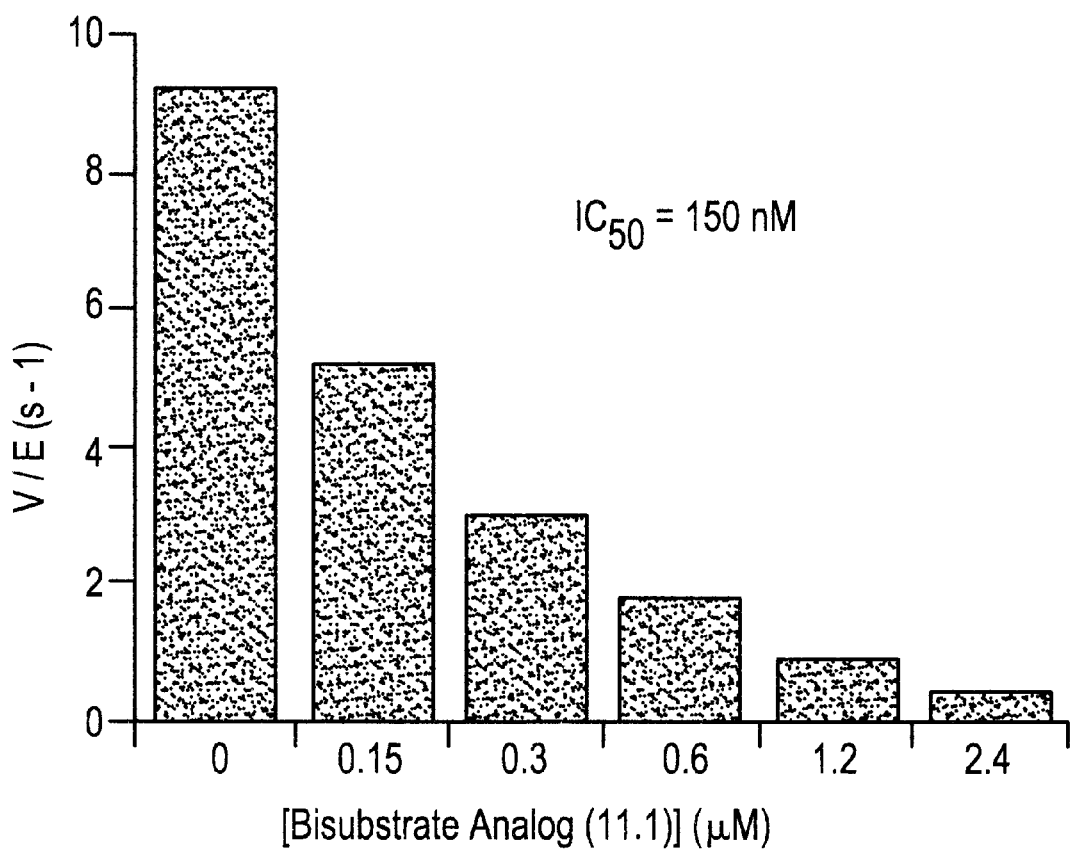
FIG. 12. Inhibition of AANAT Activity with Bisubstrate Analog 11.1
Figure 24A:
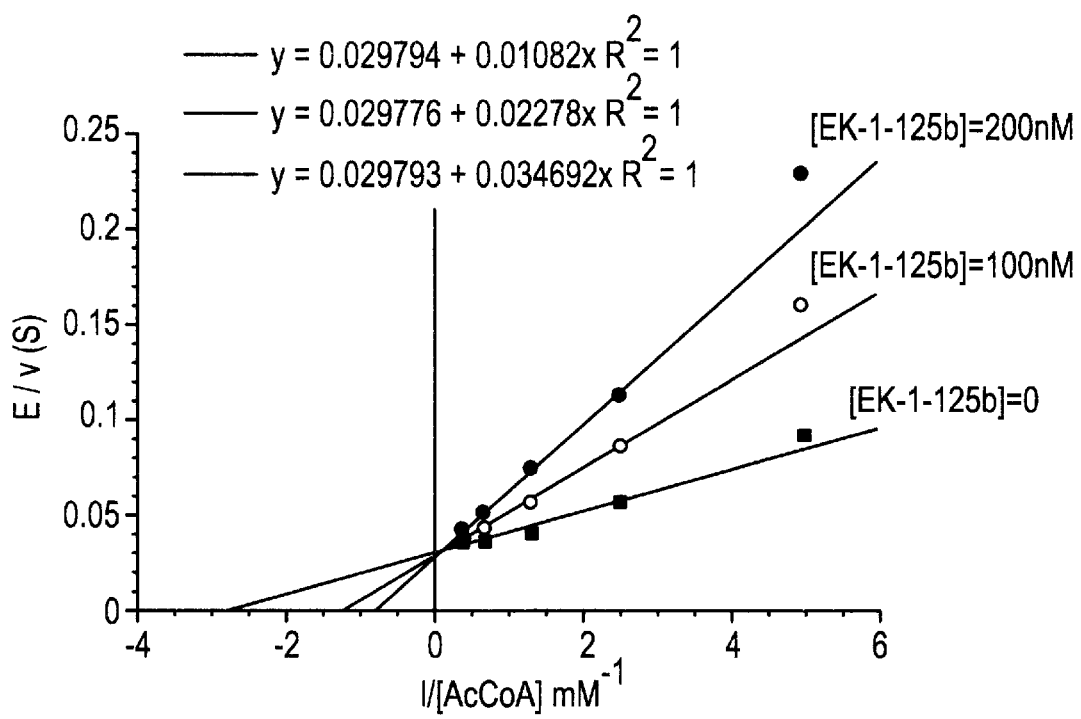
FIG. 24. Inhibition of AANAT by bisubstrate analog 11.1.
Figure 24B:
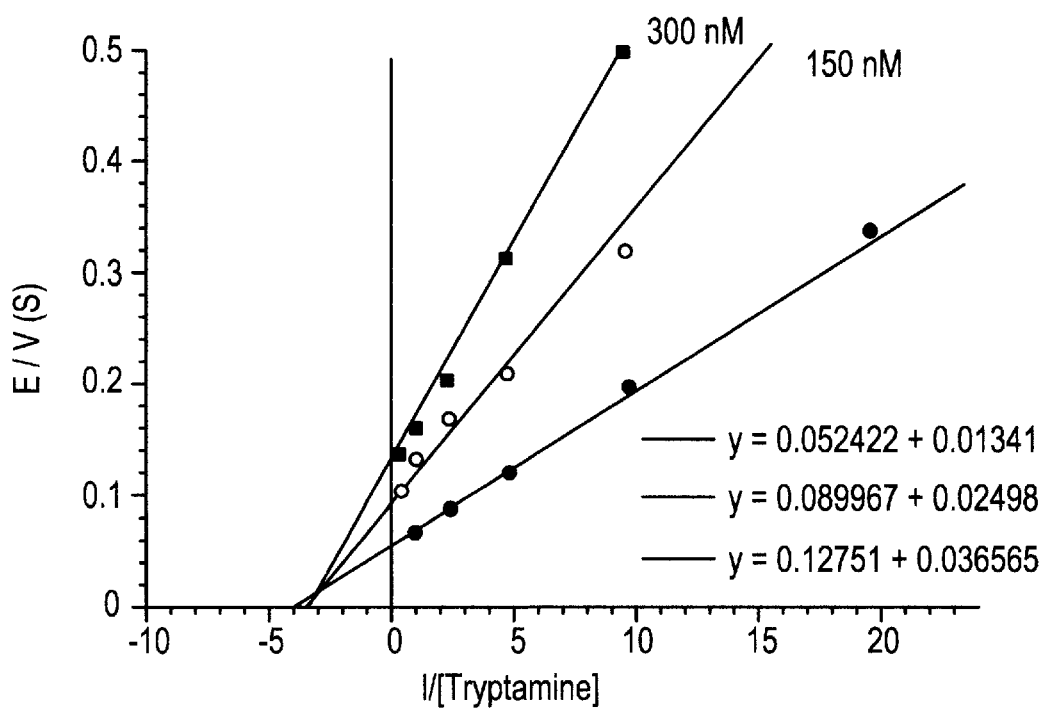
Figure 25:
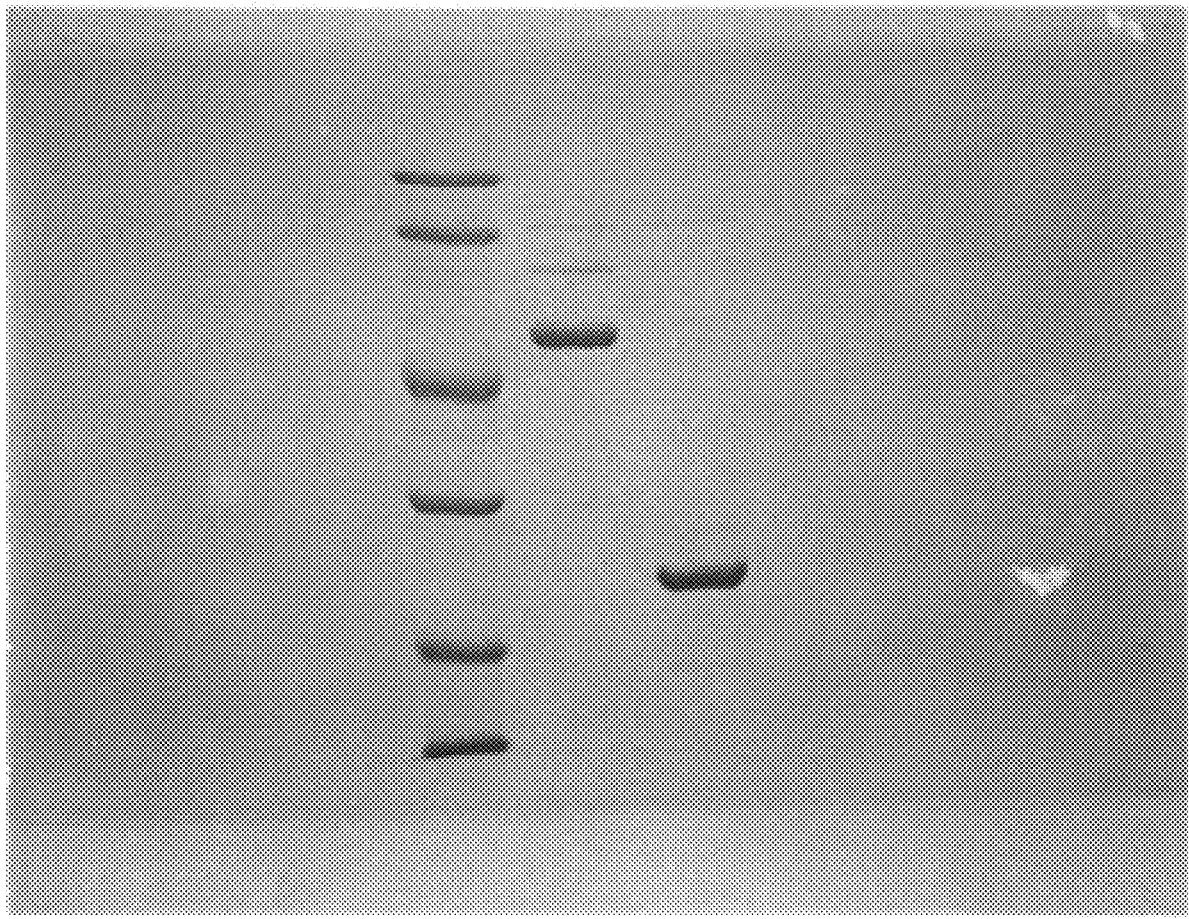
FIG. 25. 10% SDS-polyacrylamide gel electrophoresis stained with Coomassie Blue of purified GST-AANAT and AANAT proteins: From Left, first lane molecular mass markers from the top, phosphorylase b (97.4 kDA) bovine serum albumin (66.2 kDa), ovalbumin (45 kDa), carbonic anhydrase (31 kDa), soybean trypsin inhibitor (21.5 kDa). Second lane, GST-AANAT. Third lane, AANAT.
Figure 26:
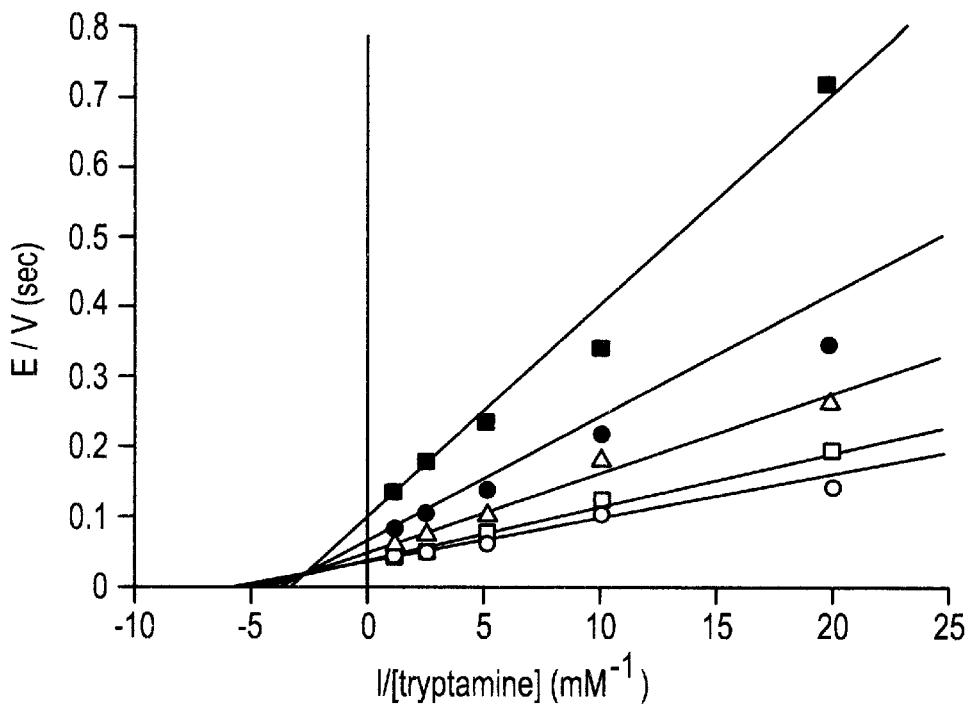
FIG. 26. 1/Velocity (E/V) versus 1/tryptamine concentration for GST-AANAT catalyzed N-acetyltransferase reaction at different acetyl-CoA concentrations: Open circles, 2 mM acetyl-CoA; Open squares 1 mM acetyl-CoA; Open triangles, 0.4 mM acetyl-CoA; Filled circles, 0.2 mM acetyl-CoA, Filled squares, 0.1 mM acetyl-CoA. The best fit was to a sequential (ternary complex) mechanism.
Figure 29:
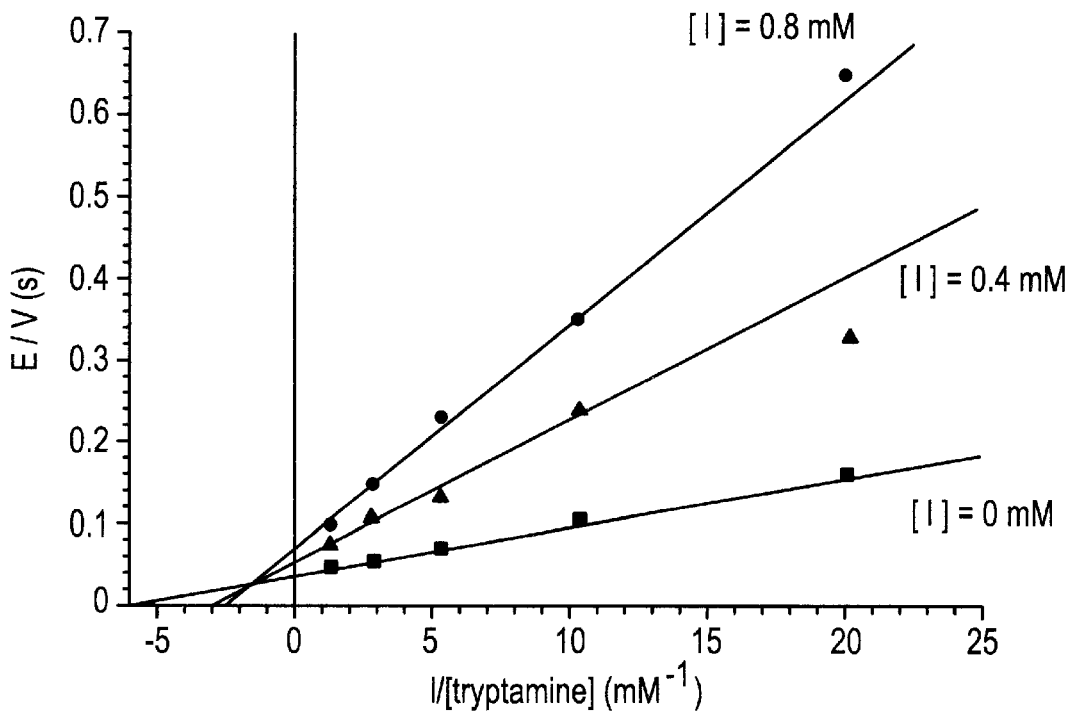
FIG. 29. 1/Velocity (E/V) versus 1/tryptamine at varying concentrations of N-acetyltryptamine (I). Acetyl-CoA concentration was fixed at 1 mM. Fit is to a linear noncompetitive inhibitor model.
Figure 27A:
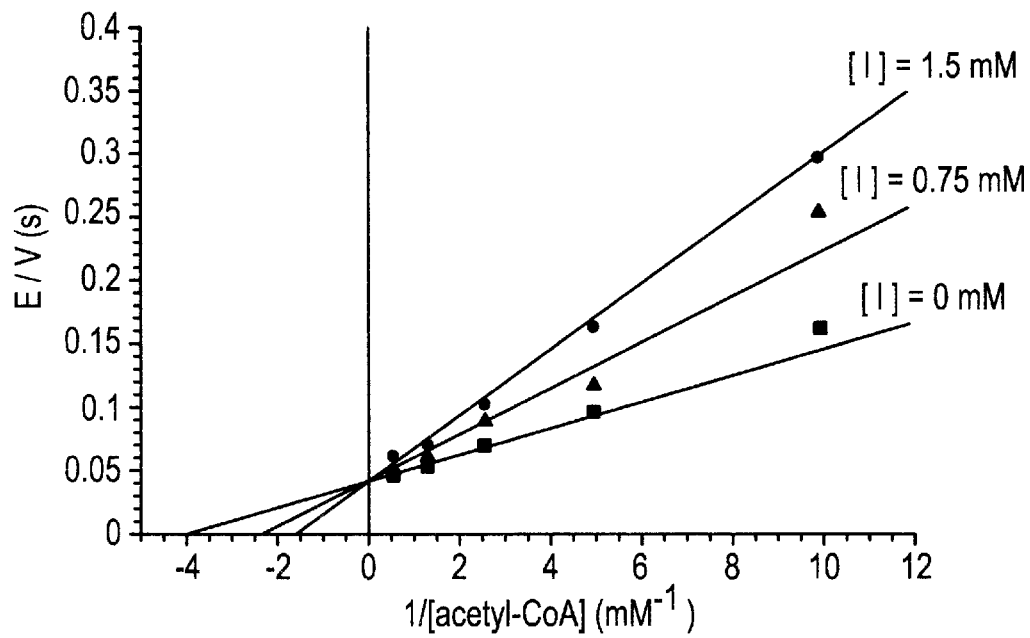
FIG. 27. Inhibition of GST-AANAT with desulfo-CoA. Panel A, 1/Velocity (E/V) versus 1/acetyl-CoA at varying concentrations of desulfo-CoA inhibotor (I). Tryptamine concentration was fixed at 1 mM. Fit is to a linear competitive inhibitor model. Panel B, 1/Velocity (E/V) versus 1/tryptamine at varying concentrations of desulfo-CoA inhibitor (I). Acetyl-CoA concentration was fixed at 0.2 mM. Fit is to a linear noncompetitive inhibitor model.
Figure 27B:
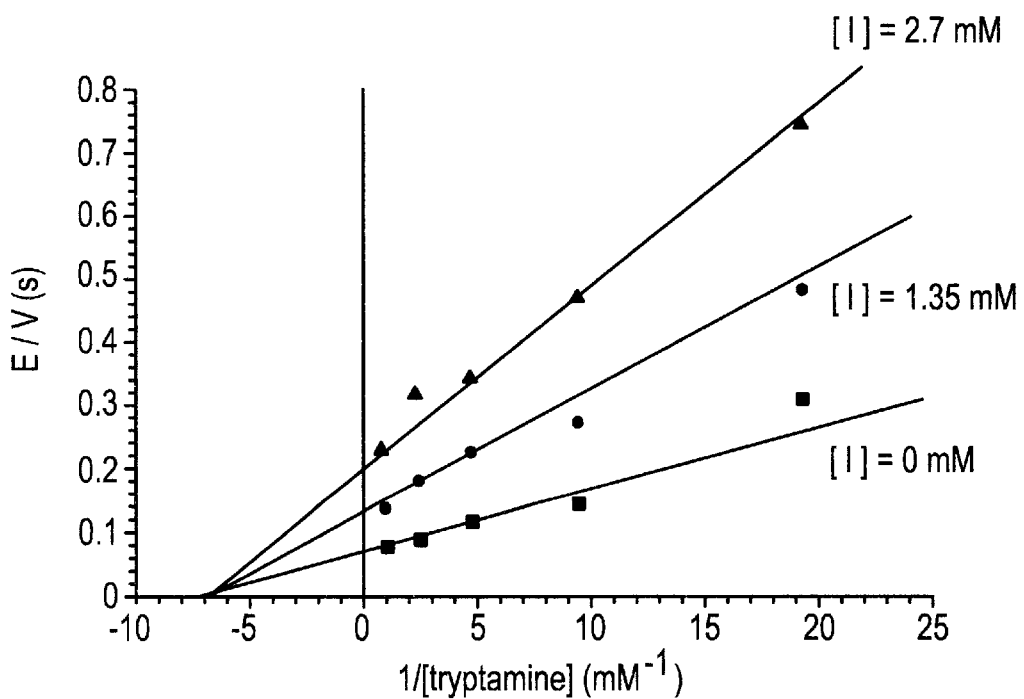
Figure 28:
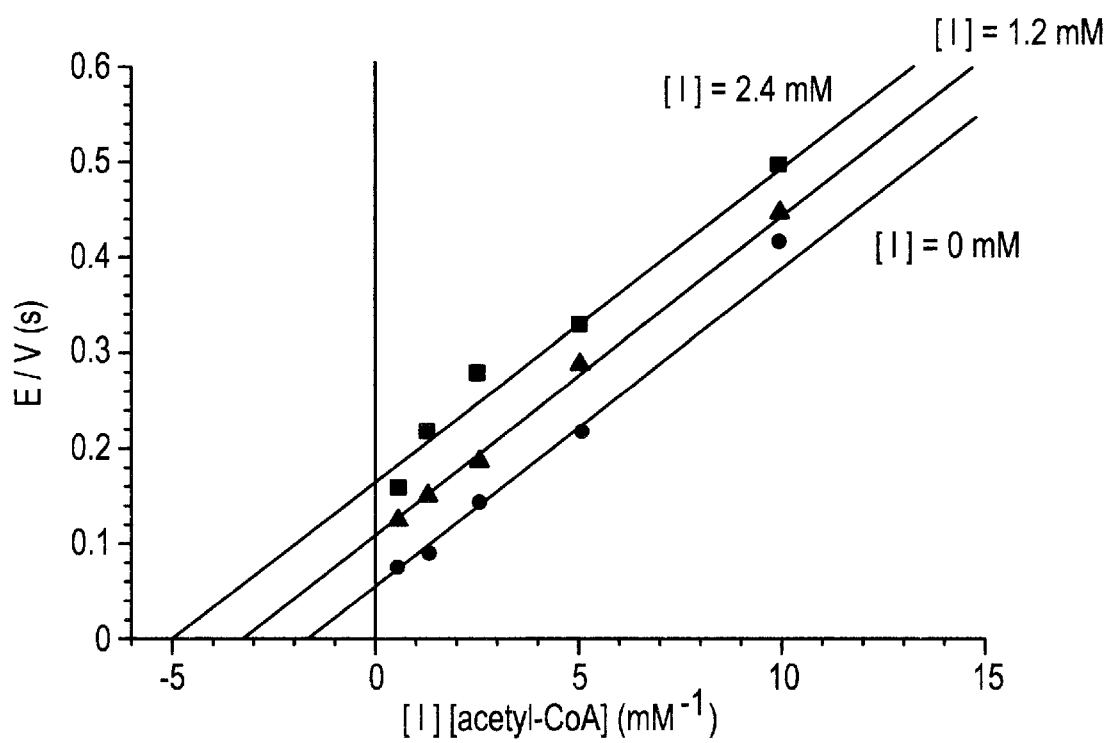
FIG. 28. 1/Velocity (E/V) versus 1/acetyl-CoA at varying concentrations of trypochol (I). Tryptamine concentration was fixed at 0.2 mM. Fit is to a linear uncompetitive inhibitor model.

Screening of X with AANAT at fixed substrate concentrations revealed it to be a very potent inhibitor of the enzyme (FIG. 12). The $IC_{50}$ (Inhibitor concentration necessary for 50% reduction in enzyme activity) was approximately 150 nM using 0.3 mM tryptamine and 0.3 mM acetyl-CoA substrate concentrations. "Rationally designed" 11.1 is the first potent AANAT inhibitor and represents an excellent lead compound for AANAT inhibitor development. A shown in FIG. 24 bisphosphate 11.1 is a potent inhibitor of serotonin N-acetyltransferase enzyme (AANAT) and its mode of inhibition is tight-binding, a reversible competitive inhibitor vs. acetyl-CoA and non-competitive inhibitor vs. tryptamine.

Experimental Design

High resolution structures of the 24 kDa protein and its complexes by NMR or X-ray crystallography were obtained. No high resolution structure of a protein from the motif A/B superfamily has been reported and obtaining such a structure would create a model for the many members of this family including the important HATs (histone acetyltransferases).

Figure 13:
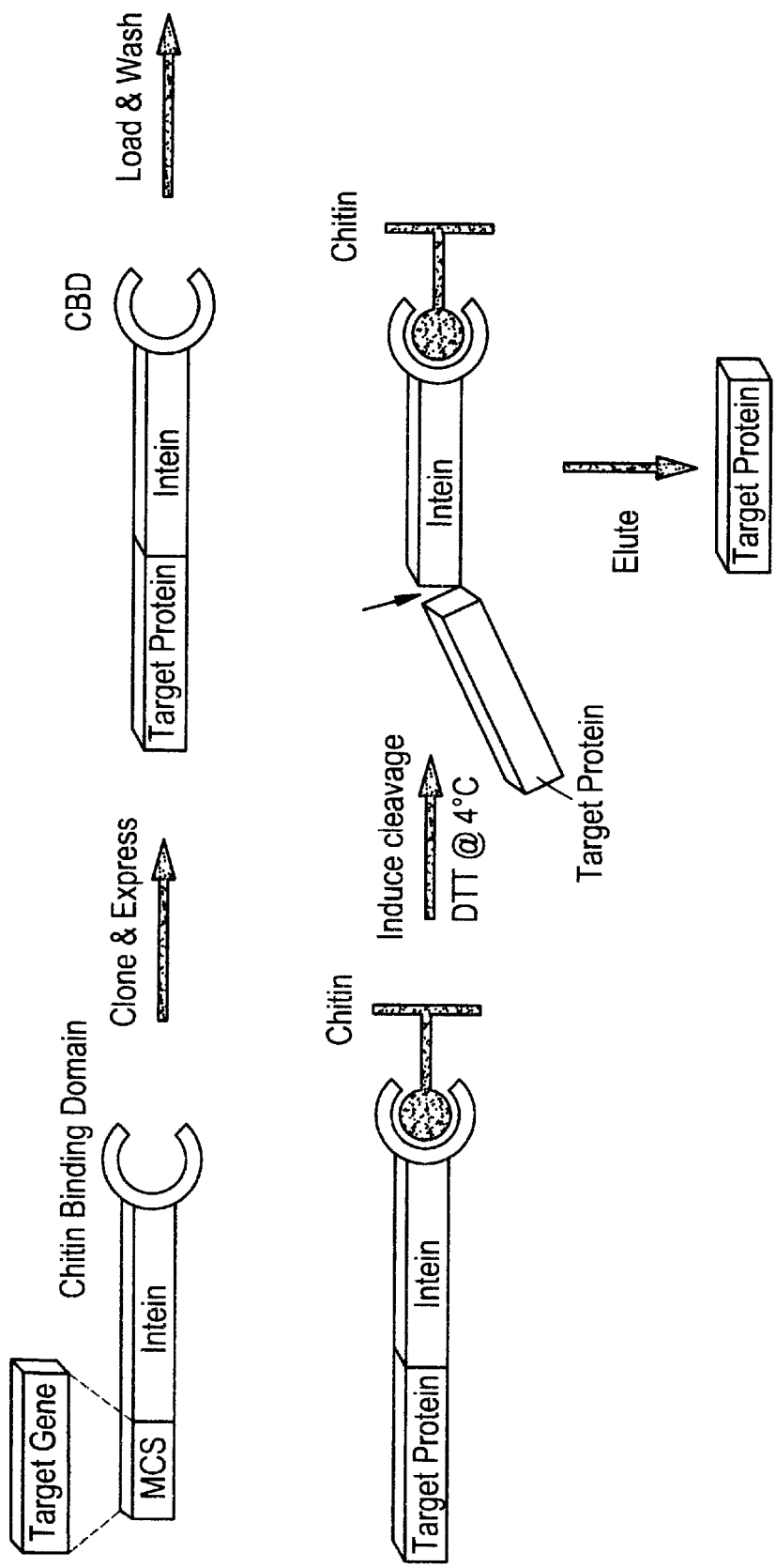
FIG. 13. IMPACT Protein Expression

Currently, sheep AANAT is produced as a GST-fusion protein. This protein is obtained in approximately 90% purity of 5–10 mg/L of culture and can be cleaved to afford the GST-free material. However, the overall yield (0.2–0.5 mg/L) and purity (80–90%) of the GST-free enzyme is insufficient, therefore, modification of the GST-fusion expression is attempted by expressing T7 in other E. coli strains including DH5a, W3110, and non-plysS strains. Alternatively, AANAT is expressed using the pET-based/T7-RNA polymerase vectors (71) or a commercially available (New England Biolabs) system called the IMPACT system which involves generating a fusion protein and then exploiting protein splicing to produce pure cleaved recombinant protein (74), the protein splicing process is initiated by the addition of a thiol reagent which cleaves a thioester in the fusion protein, liberating the protein of interest (FIG. 13). The IMPACT expression system has the strength of the fusion protein methods and contains a handle for purification (chitin binding domain) but lacks the disadvantage of requiring proteases to remove the non-native sequences.

Proteolysis/Mass Spectroscopy

One of the key difficulties in obtaining homogeneous, well-behaved proteins for NMR or X-ray studies is that certain regions in the full-length protein can interfere with overall protein behavior. If the protein contains regions that are unstructured, these can prevent crystallization of the protein. Floppy domains can cause aggregation at high concentration, leading to incompatibility with regard to NMR structure determination. Consequently, it is helpful to remove these domains if the principal protein function is not harmed. This is particularly desirable when the offending domains occur near the ends of a protein. A particularly efficient protocol and one with high predictive value to identify and remove such regions (76, 77). The method involves limited proteolysis with a non-sequence specific protease followed by mass spectrometry of the fragment(s). In general, loosely structured protein sequences show enhanced proteolytic susceptibility. These fragments can be purified by PAGE or HPLC and then characterized by molecular weight. The proteolysis/mass spec protocol will be applied to AANAT. Proteases to be screened include V8, subtilisin, trypsin, Asp-N, Lys-C, and chymotrypsin. Further information can be obtained by carrying out the proteolytic degradation in the presence of substrates or inhibitors which might lead to identification of hinge regions or those that undergo conformational changes upon substrate binding.

Optimizing AANAT Purification

The protein is purified by near homogeneity using commercially available Coenzyme A-agrose (Sigma), a preliminary study on a small scale showed that AANAT could be bound to the resin and then selectively eluted with 1 mM acetyl-CoA containing buffer. This finding is consistent with the mechanistic model that acetyl-CoA is the first substrate to bind in the enzymatic reaction. Further purification will be carried out using FPLC using both cation (MonoS) and anion (MonoQ) methods as well as size exclusion and hydrophobic chromatographies until >97% purification is achieved.

A full understanding of the AANAT catalytic mechanism is a key component of efforts toward rational inhibitor design. It will also provide a framework for how the motif A/B enzyme superfamily achieve catalysis including the important HAT enzymes.

Nature of the AANAT Reaction Intermediates

The steady-state kinetic data support a model with an ordered Bi Bi sequential mechanism where acetyl-CoA binds to the enzyme prior to serotonin and a ternary complex is formed followed by the product release steps of N-acetylserotonin and CoASH. Although the kinetic data allow the generation of a reasonable model, other complimentary experiments are necessary to test the validity of the proposal and provide more quantitative detail about the nature of the intermediates.

Chemical Nature of the Transition State

Elucidating the nature of the transition state is important for understanding the enzymes. To facilitate acyl transfer, the serotonin ammonium nucleophile is deprotonated to the neutral amine. This is accomplished by lowering the $pK_a$ of the amine upon binding to the enzyme, or by a concerted process where deprotonation occurs in the same step as attack on the carbonyl (87). Thus the transition state may or may not have positive charge on the nitrogen in the transition state.

To address these details, pH-rate analyses, isotope effect measurements, substrate analog studies, and $^{15}N$-NMR-$pK_a$ titrations is carried out. A pH-rate study of $k_{cat}$ and $k_{cat}/K_m$ provides indirect information about whether one or more groups that have $pK_a$'s that are important in catalysis have pKa's in the pH 6–9 range. Effects on $k_{cat}$ correlate with the substrate-bound form of the enzyme whereas effects on $k_{cat}/K_m$ correspond to the free enzyme form (88). Studies with Nw-methyltryptamine, a poor substrate with chemistry rate-determining and tryptamine a good substrate in which product release is rate-determining provides complementary information.

Figure 14:
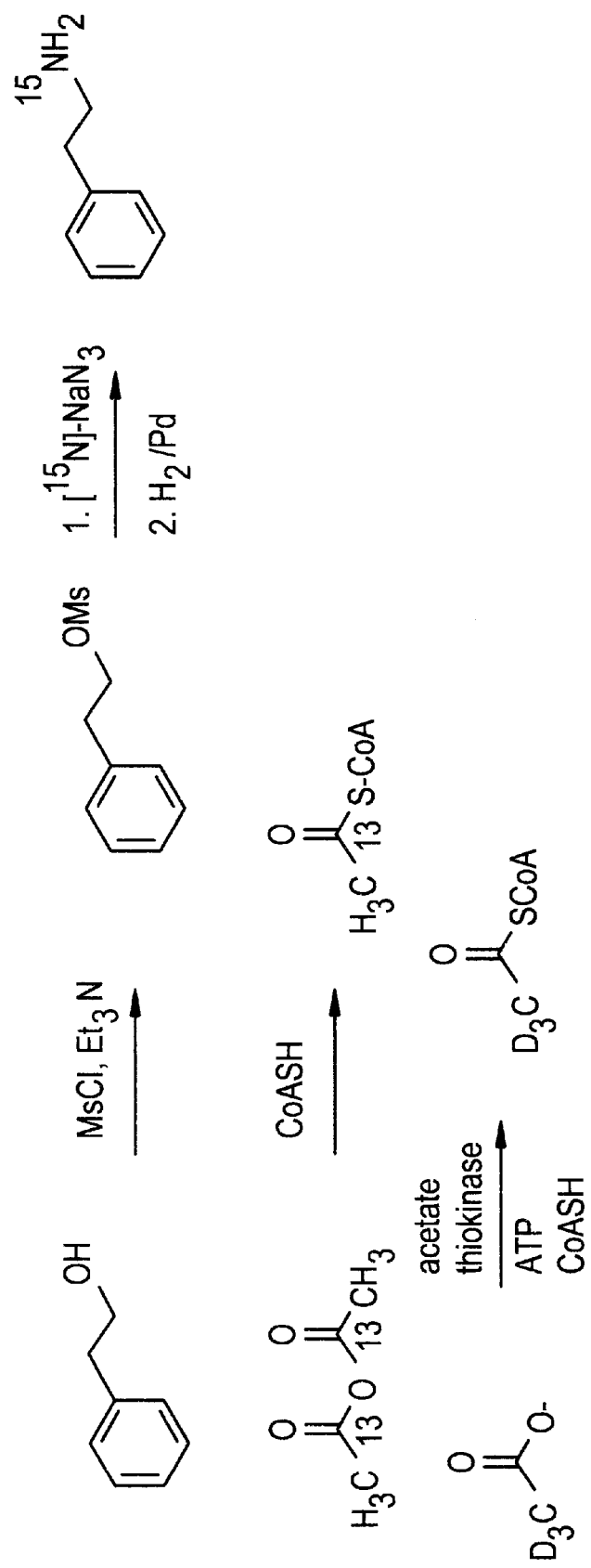
FIG. 14. Synthetic Approaches Toward Isotopically Labelled Substrates
Figure 15:
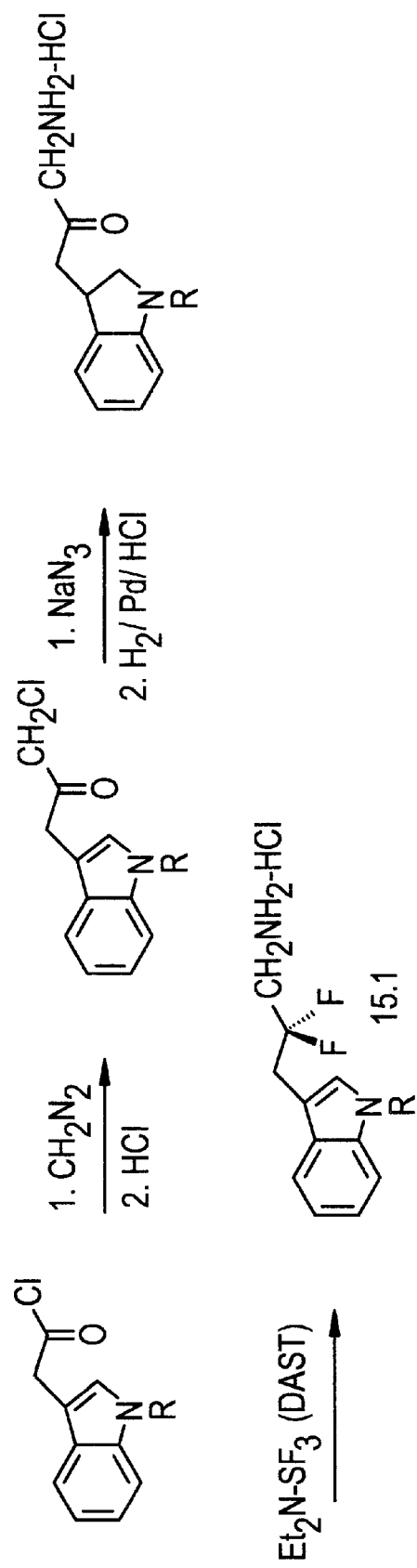
FIG. 15. Synthetic Approach to difluoropropylamino derivatives 15.1

The role of proton transfer in the transition state is assessed in principle with solvent isotope effects (89, 90). The compounds used in these experiments is synthesized as shown below (FIG. 14) (93). Ya-Trifluoromethyltryptamine was shown not to be a substrate and this can be interpreted as evidence that the nucleophilicity of the amine is important. To follow-up on this result, the corresponding mono and difluoro-compounds is synthesized (using a method analogous to that shown in FIG. 9) as well as the fluoroproylamine derivative 15.1 (synthetic approach in FIG. 15)(94–97).

Figure 16:
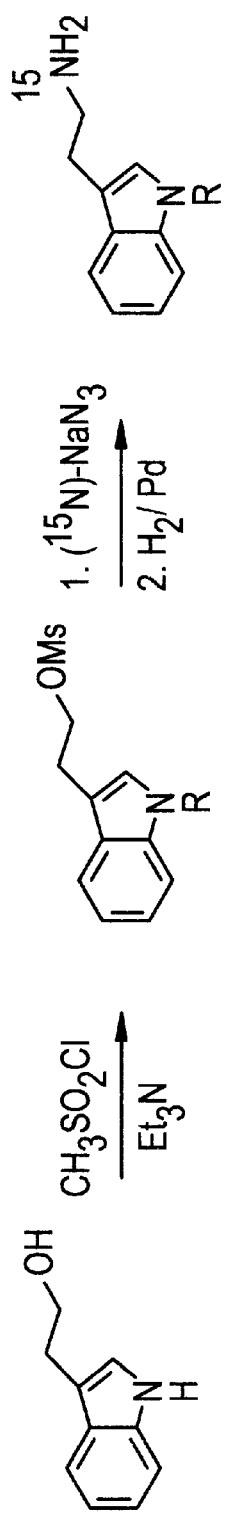
FIG. 16. Synthetic Approach to $^{15}$N-Labelled Tryptamine

Titration of the chemical shift vs. pH of the tryptamine primary amine bound to the enzyme allows a direct analysis of the $pK_a$ of the amine in the active site (98, 99). Synthesis of $^{15}N$-tryptamine is carried out as shown in the scheme below (FIG. 16).

Pre-steady-state Kinetics

Figure 17:
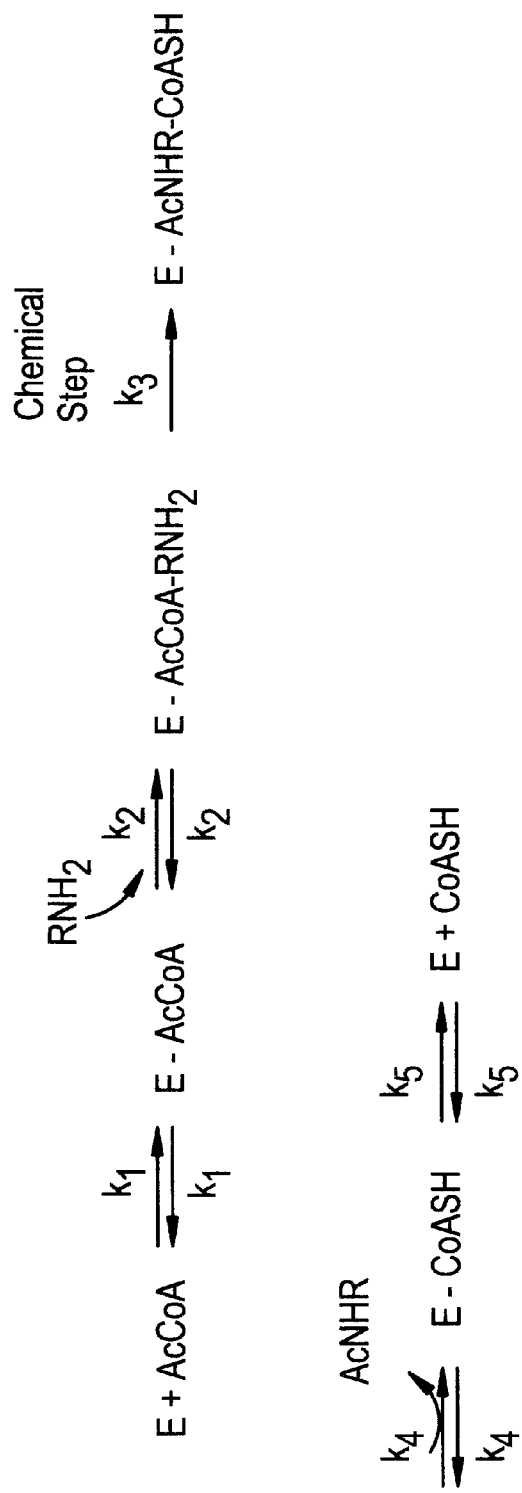
FIG. 17. Ordered BiBi Mechanism for AANAT

The key rate constants are i) the rate of acetyl-CoA binding ($k_1$); ii) the rate of serotonin binding ($k_2$); iii) the rate of the chemical step ($k_3$); iv) the rate of release of N-acetylserotonin (N-acetyltryptamine) ($k_4$) and the rate of release of CoASH ($k_5$) (see FIG. 17). Viscosity measurements have given indirect information about the chemical step rate which is estimated to be $>60\ s^{-1}$. Thus, the reaction can be initiated and quenched within milliseconds after mixing and the rate of products can then be quantitated. In principle, this can give a direct chemical rate because in the first turnover, product release will not contribute to the kinetics. Thus a "burst phase" resulting in the build-up of N-acetyltryptamine (and CoASH) still bound to the enzyme can be quantified after denaturing the enzyme with acid, base, organic solvents, or detergent. The magnitude of the burst phase should correlate with the amount of AANAT in the experiment. These experiments is carried out with 1–10 mM AANAT (or GST-AANAT) employing [$^{14}C$]-acetyl-CoA. [$^{14}C$]-N-acetyltryptamine product is quantitated by extraction into organic solvent and radioactive quantitation will follow HPLC or TLC. Controls with "poor substrates" such as Nw-methyltryptamine where no burst phase is expected is carried out for comparison.

Identification of Active Site Residues Important for Catalysis

Figure 18:
FIG. 18. Affinity Labels

While there is no substitute for a high resolution structure to help identify active site residues, prior to obtaining this structure and subsequent to its acquisition, a combination of site-directed mutagenesis, group modifying reagents, and affinity labelling is carried out to identify key enzymatic residues. The first amine acid whose role is probed in histidine. Thus, it has been speculated that an imidazole of a histidine might be important in catalysis in AANAT based on two pieces of experimental evidence (45). First, the induction of AANAT in the pineal is blocked if 2-fluorohistidine replaces histidine and second, mutation of His-110 to Gln has been reported to abolish activity. Neither of these experiments is definitive. The former was performed in vivo where many effects of 2-fluorohistidine are possible. As AANAT is very unstable in the absence of reducing agents. Thus iodoacetamide labelling of the protein is carried out to see if a specific cysteine is selectively labelled. It is possible that such cysteines would not be active site related so again substrate protection and pH-rate profiles is carried out to determine the $pK_a$ of inactivation. A complementary approach is taken with affinity labels (101) based on the two substrates. In particular bromacetamide analogs of CoA (68) and tryptamine (FIG. 18) is tried first. It is plausible that these may inactivate the enzyme on catalytically important residues in the active site. Substrate protection experiments and pH-rate profiles of inactivation will also be carried out. After labelling the enzyme, tryptic digest and Edman/mass spec analysis is carried out to identify the involved residue(s).

Comparison to other Motif A/B Acetyltransferases

Little is known about the structure or mechanism of other motif A/B family members despite their biological importance. Thus, the aminoglycoside acetyltransferases important in antibiotic resistance (102, 103) and PCAF histone acetyltransferase (50) postulated to regulate gene expression are in this family. The overproduction and purification of these.

Design, synthesize, and evaluate novel serotonin N-acetyltransferase inhibitors

Potent inhibitors of serotonin N-acetyltransferase serve as biological tools that help reveal biological functions for melatonin and pineal serotonin in vivo. Ultimately, they could even serve as therapeutic agents for a variety of different conditions (perhaps by allowing pineal serotonin and melatonin to be artificially regulated). A synthetic bisubstrate compound (11.1) which incorporated the indole and coenzyme A moieties of the two substrates was an extremely potent AANAT inhibitor. The $IC_{50}$ of 150 mM is near the expected range to be effective for in vivo studies.

Kinetic and Biophysical Characterization of Bisubstrate Inhibitor (11.1) with AANAT Little is yet known about the detailed kinetic mode of inhibition of AANAT by 11.1. For example, the material may be a conventional reversible inhibitor or it may exhibit "slow-binding" behavior (104). A bisubstrate inhibitor of carnitine acetyltransferase has been reported to show a slow-binding form of inhibition. Thus "slow-binding" inhibition can result from a slow conformational change that must occur to achieve tight-binding. Under these circumstances, the off-rate of the inhibitor may be extremely slow and appear to be irreversible. Both $K_i$ (standard reversible binding constant) and $K_i^*$ (tight-binding constant) are necessary to describe inhibition of this type (104). To carry out these studies, pre-incubation of the enzyme with the inhibitor for varying lengths of time may be necessary. As such, a radioactive acetyltransferase assay (so that thiol reducing agents are present for stability) can be employed. If slow-binding inhibition is observed kinetically, it will provide even greater impetus for structural studies of the inhibited enzyme and to compare the inhibited structure to the free enzyme.

If the compound behaves as a more standard reversible inhibitor, a kinetic assessment of its inhibitory characteristics versus varying concentrations of the substrates tryptamine and acetyl-CoA is carried out. Because of its structure, the expectation is that in double reciprocal plots it will show slope effects versus both substrates and possibly intercept effects against one or both substrates (60). A detailed steady-state kinetic characterization could provide information about how the inhibitor is actually working and is a pre-requisite to investigating effects of ionic strength and pH. Thus, it is unclear how much of the inhibitor 11.1 binding is sensitive to electrostatic interactions (and thus would be highly salt sensitive) and how much is due to non-ionic interactions. Likewise, a pH tritration of the $K_i$ is of value in identifying the $pK_a$ of group(s) that contribute to the high affinity of interaction.

Arylamine acetyltransferase, which catalyzes the transfer of the acetyl group from acetyl-CoA to a variety of aromatic amines (including serotonin) is tested. Unlike AANAT, arylamine acetyltransferase follows a ping-pong mechanism and thus would not be expected to bind simultaneously to CoA and the amine substrate. Thus the bisubstrate inhibitor 11.1 would not be expected to be a potent inhibitor of arylamine acetyltransferase. Currently, no such reagents exist for definitely quantitating AANAT activity in crude pineal extracts.

Testing the bisubstrate analog 11.1 as an inhibitor is carried out using commercially available (Sigma) pigeon liver arylamine acetyltransferase. Similarly concentrations of the substrates nitroaniline and acetyl-CoA is used as tryptamine and acetyl-CoA with AANAT in the presence of varying inhibitor concentrations.

Two members of the motif AB actyltransferase superfamily are also screened with the inhibitor 11.1, aminoglycoside acetyltransferase and PCAF histone acetyltransferase. Although these enzymes may follow ternary complex mechanisms, the amine substrate is quite different and thus relatively weak inhibition would be expected compared to AANAT.

Tether and functionality requirements in the bridge

Figure 19:
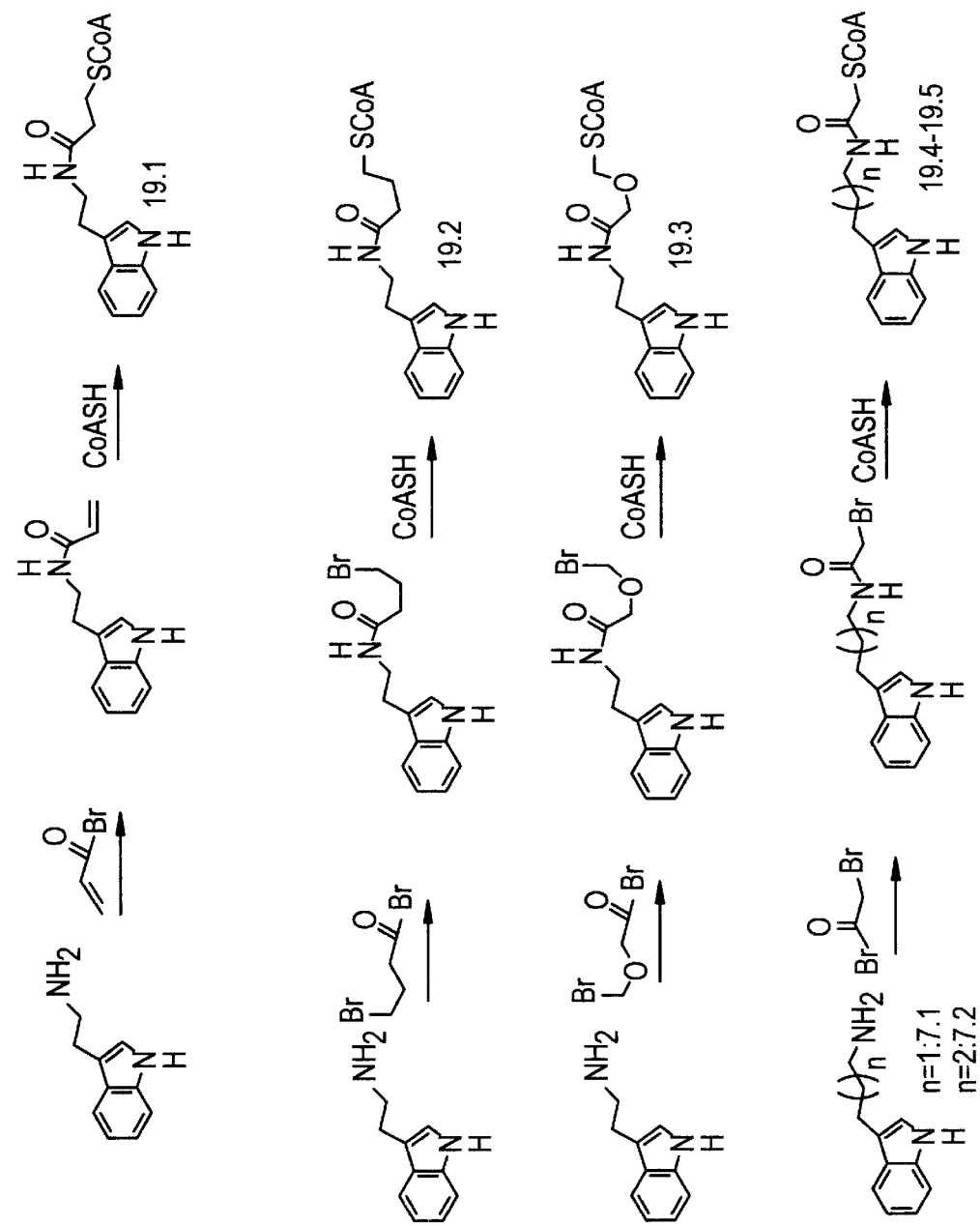
FIG. 19. Synthetic Approaches to Varying Length Tethered Bisubstrate Analogs

In addition to the quantitative studies described above for the bisubstrate compound 11.1, a general analysis of the tether length and bridging functionality is pursued. Thus the distance between the indole and coenzyme A optimal for binding, which may reflect the transition state distance between the substrates, is analyzed with different tethers. In the first series of compounds (FIG. 19), the tether length is varied with alkyl chains containing two to six carbons. These compounds is synthesized according to the plan shown in FIG. 19. In addition, an oxygen atom substitution in the all carbon linker is performed in order to assess the role of linker hydrophobicity. If longer linkers are superior, further refinements can be made such as introducing rigidity to the tether by alkyl substitution or cyclization.

Figure 20:
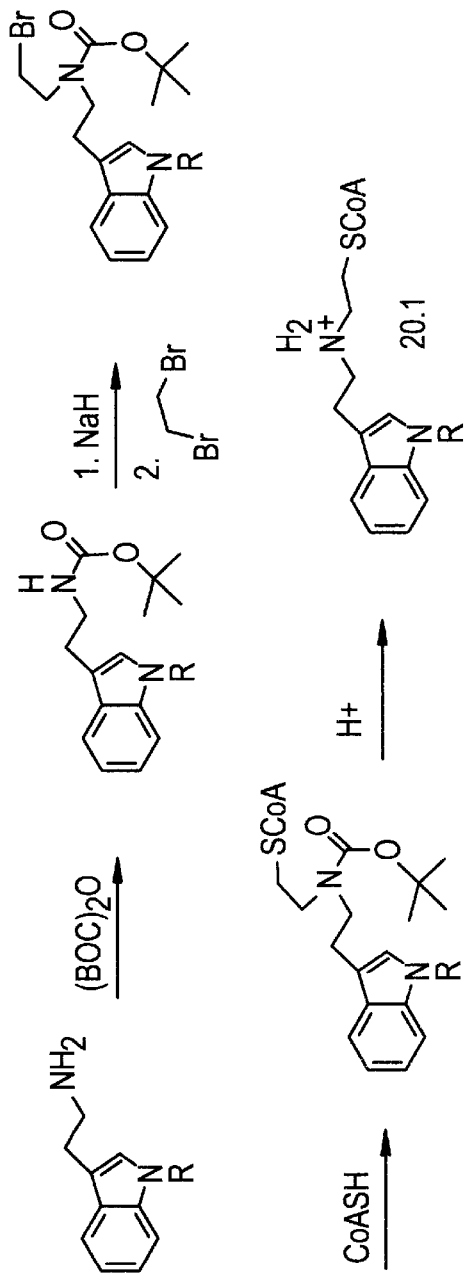
FIG. 20. Synthetic Approach Toward Bisubstrate Analog (20.1)

Another issue to be explored in optimizing bisubstrate AANAT inhibitors concerns the role of charge and electronegative substitution in the linker. The nitrogen atom of the amine substrate may optimally be positively charged for binding. Thus increased affinity may be obtained by eliminating the carbonyl oxygen from the linker as exemplified by analog 20.1. Removal of the carbonyl oxygen may prevent steric/electronic clash and allows the nitrogen to be positively charged at neutral pH like tryptamine itself. If this is the case, it could potentially form a salt bridge or tighter hydrogen bond with an AANAT residue. Synthesis of this compound is envisaged to proceed as shown in FIG. 20.

Figure 21:
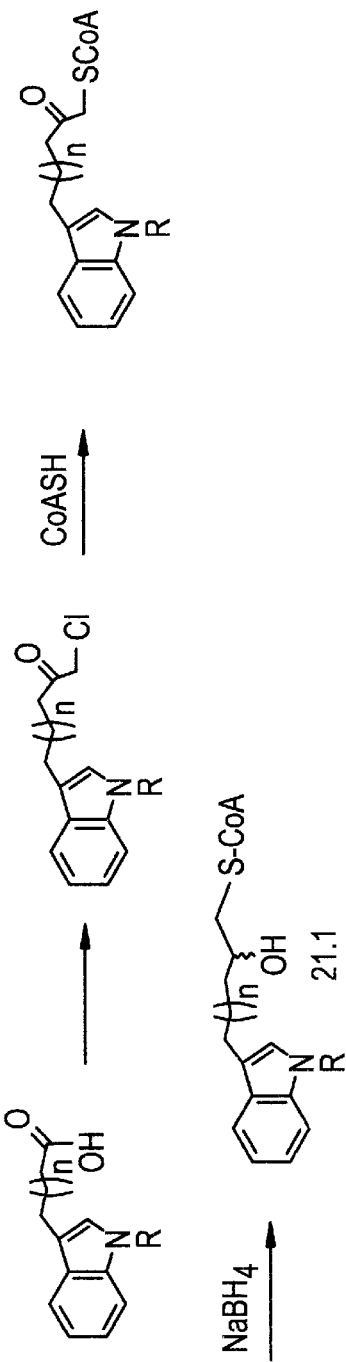
FIG. 21. Synthetic Approach to Tetrahedral Bisubstrate Analog 21.1
Figure 22:
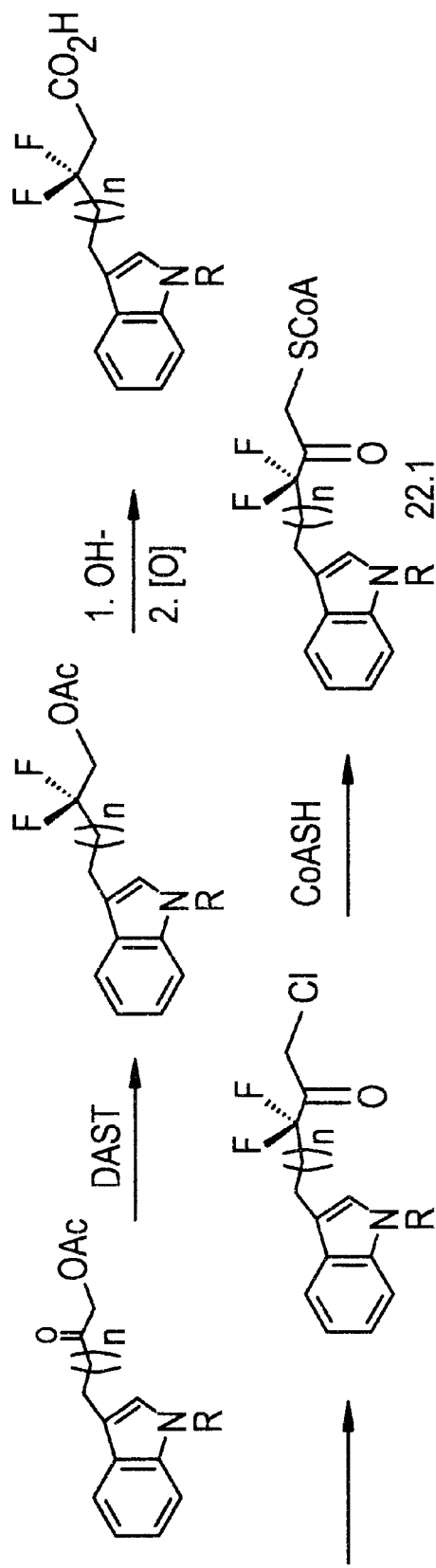
FIG. 22. Synthetic Approach to Bisubstrate Analogs 22.1

Another feature that might improve affinity is to mold the tether into a tetrahedral transition state mimic. This strategy has been very successful in protease inhibition (104). Thus if pyramidalization of the carbonyl is important, interesting compounds might have an $sp^3$ alcohol (21.1) or a gem-diol like substituent as would be prone to form with difluoroketone analog (22.1) in the bridging region. Synthetic approaches toward these compounds are depicted in FIGS. 21 and 22 (94–97).

Variations in the tryptamine and CoA moieties of 11.1

In addition to efforts designed to examine the role of the linker region of the bisubstrate analog inhibitor 11.1, an investigation of substitutions/deletions in the tryptamine and CoA moieties is undertaken. Although tryptamine is a comparably good substrate to serotonin in the reaction, it is possible that the hydroxy group might affect affinity of the bisubstrate inhibitor in the context of a transition state analog inhibitor. In addition, other commercially available tryptamine analogs including 6-fluorotryptamine, 5-methyltryptamine, Nw-methyltryptamine, and a-methyltryptamine is tested. At this point, it is not clear how essential the indole function is in these inhibitors. That is, it is possible that other large hydrophobic molecules can fill its role as well. To evaluate this requirement, a series of hydrophobic -CoA analogs is made and evaluated as inhibitors. The commercially available fatty acyl-CoA derivatives is investigated first. These compounds which have from 8–18 carbons in the fatty acid could potentially fill the a hydrophobic pocket as well as an indole. Depending on the outcome of these studies, phenethylamine and related aromatic analogs is also be tested.

Figure 23:
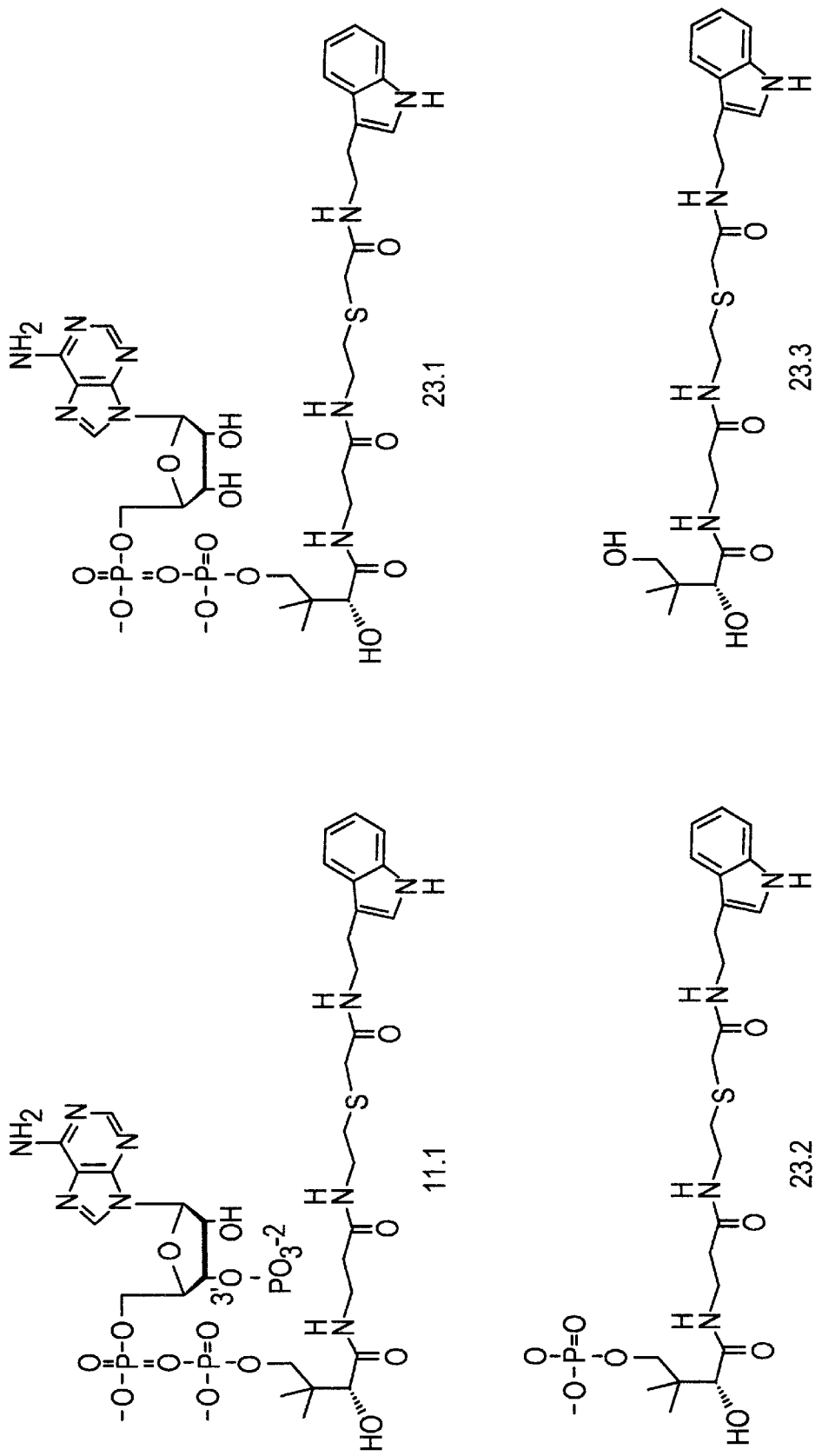
FIG. 23. Bisubstrate Analogs with Variations on the CoA Substructure

The bisubstrate analog lacking this phosphate 23.1 (FIG. 23) is prepared by reacting the commercially available dephosopho-CoASH with the tryptamine bromoketone. In addition, the bisubstrate analog containing phosphopantetheine 23.2 and pantetheine 23.3 is prepared in analogous fashion. It is likely that the neutral derivatized pantetheine 23.3 can enter cells and so even if the analog is not in itself an inhibitor in vitro, it could be reasonably expected to be a pro-drug getting processed in the cytosol to the CoA derivative. Based on how these studies proceed, more extensive dissection of the CoA functionalities critical for in vitro efficacy is carried out. It should also be mentioned that if analogs 22.2 and 22.3 are not potent in vitro AANAT inhibitors by themselves, supplemental AMP and ADP is added concomitant with the testing of these inhibitors. Thus occupation of the nucleotide cavity may be key to bringing out their inhibitory potential. If these approaches are unsuccessful, uncharged bridges can be synthetically incorporated between the adenosine and pantetheine moiety to facilitate cell entry.

REFERENCES

1) McCord, C. P., Allen, F. P. (1917) *J. Exp. Zool*, 23, 107.
2) Lerner, A. B., Case, J. D., Takahashi, Y., Lee, T. H., Mori, W. (1958) Isolation of melatonin, pineal factor that lights melanocytes. *J. Am. Chem. Soc.* 80, 2587.
3) Lerner, A. B., Case, J. D., Heinzelman, R. V. (1959) Structure of melatonin *J. Am. Chem.* 81, 6084–6085.
4) Vaughan, G. M., Pelham, R. W., Pang, S. F., Loughlin, L. L., Wilson, K. M., Sandock, K. L., Vaughan, M. K., Koslow, S. H., Reiter, R. J. (1976) Nocturnal elevation of plasma melatonin and urinary 5-hydroxyindoleactic acid in young men: attempts at modification by brief changes in environmental lighting and sleep and by autonomic drugs. *J. Cin. Endocrinol. Metab.* 42, 752–764.
5) Arendt, J. (1995) 'Melatonin and the mammalian pineal gland', Chapman and Hall, New York.
6) Binkley, S. (1988) 'The pineal: endocrine and nonendocrine function', Prentice Hall, New Jersey.
7) Liu, C., Weaver, D. R., Strogatz, S. H., Reppert, S. M. (1997) Cellular construction of a circadian clock: period determination in the suprachiasmatic nuclei. *Cell* 91, 855–860.
8) Marsden, C. A. (1996) The neuropharmacology of serotonin in the central nervous system. *Perspectives in Psychiatry Vol 5* (*Selective serotonin re-uptake inhibitors*, edited by Feighner, J. P., Boyer, W. F.; Wiley, New York, 1–33.
9) Cagnacci, J., Elliot, J., Yen, S. (1992) Melatonin: a major regulator of the circadian rhythm of core temperature in humans. *J. Clin. Endocrinol. Metab.* 75, 447–452.

10) Akerstedt, T., Froberg, J. E., Friberg, W., Wetterberg, L. (1979) Melatonin excretion, body temperature and subjective arousal during 64 hours of sleep deprivation. *Psychoneuroendocrinology* 4, 219.
11) Roenneberg. T., Aschoff, J. (1990) Annual rhythms in human reproduction: I. Biology, sociology or both? *J. Biological Rhythms.* 5, 195–216.
12) Tamarkin, "K., Baird, C. J., Almeida, O. F. X. (1995) Melatonin: a coordinating signal for mammalian reproduction. *Science* 227, 714–720.
13) Waldhauser, F., Weiszenbacher, G., Frisch, H., Zeitlhuber, U., Waldhauser, M., Wurtman, R. J., (1984) Fall in nocturnal serum melatonin during prepuberty and pubescence. *Lancet* i, 362–365.
14) Iguch, H., Kato, K., Ibayashi, H. (1982) Age-dependent reduction in serum melatonin concentrations in healthy human subjects. *J. Clin. Endocrin. Metabl.* 55, 27, 1982.
15) Lewinski, A., Zelazowski, P., Sewerynek, E., Zerek-Melen, G., Szkudlinski, M., Zelazowska, E. (1989) Melatonin-induced suppression of human lymphocyte natural killer activity in vitro. *J. Pineal Research* 7, 153–164.
16) Maestroni, G. J., Conti, A., Pierpaoli, W. (1988) Role of the pineal gland in immunity. III. Melatonin antagonizes the immunosuppressive effect of acute stress via an opiatergic mechanism. *Immunology* 63, 465–469.
17) Sparks. D. L., Hunsaker, J. C., (1988) III. The pineal gland in sudden infant death syndrome: preliminary observations. *J. Pineal Research* 5, 111–118.
18) Sturner, W. Q., Lynch, H. J., Deng, M. H., Gleason, R. E., Wurtman, R. J. (1990) Melatonin concentrations in the sudden infant death syndrome. *Forensic Science International* 45, 171–180.
19) Harlow, H. J. (1987) Influence of the pineal gland and melatonin on blood flow and evaporative water loss during heat stress in rats. *J. Pineal Research* 4, 147–159.
20) Steindl, P. E., Finn, B., Bendok, B., Rothke, S., Zee, P. C., Blei, A. T. (1995) Disruption of the diurnal rhythm of plasma melatonin in cirrhosis. *Ann. Int. Med.* 123, 274–277.
21) Lewy, A. J., Sack, R. L., Miller, L. S., Hoban, T. M. (1987) Anti-depressant and circadian phase-shifting effects of light. *Science* 235, 352–354.
22) Sack, R. L., Lewy, A. J., Blood, M. L., Keith, L. D., Nakagawa, H. (1992) Circadian rhythm abnormalities in totally blind people: incidence and clinical significance. *J. Clin. Endocrinol. Metab.* 75, 127–134.
23) Arendt, J., Bhanji, S., Franey, C., Mattingly, D. (1992) Plasma melatonin levels in anorexia nervosa. *British J. Psychiatry* 161, 361–364.
24) Cohen, M., Lippman, M., Chabner, B. (1978) Role of pineal gland in aetiology and treatment of breast cancer. *Lancet* ii, 814–816.
25) Reppert, S. M. & Weaver, D. R. (1995) "Melatonin madness" *Cell* 83, 1059–1062.
26) Cassone, V. (1992) The pineal gland influences rat circadian activity rhythms in constant light. *J. Biol. Rhythms* 7, 27–40.
27) Redman, J., Armstrong, S., Ng, K. T. (1983) Free-running activity rhythms in the rat: entrainment by melatonin. *Science* 219, 1089–1091.
28) Arendt, J., Borbely, A. A., Franey, C., Wright, J. (1984) The effect of chronic, small doses of melatonin given in the late afternoon on fatigue in main: a preliminary study. *Neuroscience Letters* 45, 317–321.
29) Rivkees, S. A., Carlson, L. L., Reppert, S. M. (1989) Guanine nucleotide-binding protein regulation of melatonin receptors in lizard brain. *Proc. Natl. Acad. Sci. USA* 86, 3883–3886.
30) Reppert, S. M., Weaver, D. R., Ebisawa, T. (1994) Cloning and characterization of a mammalian melatonin receptor that mediates reproductive and circadian responses. *Neuron* 13, 1177–1185.
31) Reppert, S. M., Godson, C., Mahle, C. D., Weaver, D. R. Slaugenhaupt, S. A., Gusella, J. F. (1995) Molecular characterization of a second melatonin receptor expressed in human retina and brain: the $Mel_{1b}$ melatonin receptor. *Proc. Natl. Acad. Sci. USA* 92, 8734–8738.
32) Wisenberg. I., Missbach, M., Kahlen, J.-P., Schrader, M., Carlberg, C. (1995) Transcriptional activation of the nuclear receptor RZRa by the pineal gland hormone melatonin and indentification of CGP 52608 as a synthetic ligand. *Nuc. Acids Res.* 23, 327–333.
33) Steinhilber. D., Brungs, M., Werz, O., Wisenberg, I., Danielsson, C., Kahlen, J.-P., Nayeri, S., Schrader, M., Carlberg, C. (1995) Nuclear receptor for melatonin represses 5-lipoxygenase gene expression in human B lymphocytes" *J. Biol. Chem.* 270, 7037–7040.
34) Aldhous, M., Franey, C., Wright, J., Arendt, J. (1985) Plasma concentrations of melatonin in man following oral absorption of different preparations. *Br. J. Clin. Pharmacol.* 19, 517–521.
35) Sugden, D. (1983) Psychopharmacological effects of melatonin in mouse and rat *J. Pharmacol. Exp. Ther.* 22, 587–591.
36) D'Sa, C. M., Arthur, R. E., States, J. C., Kuhn, D. M. (1996) Tryptophan hydroxylase: cloning and expression of the rat brain enzyme in mammalian cells. *J. Neurochem.* 67, 900–906.
37) Albert, V. R., Lee. M. R., Bolden, A. H., Wurzburger, R. J., Aguanno, A. (1992) Distinct promoters direct neuronal and nonneuronal expression of rat aromatic L-amino acid decarboxylase. *Proc. Natl. Acad. Sci. USA* 89, 12053–12057.
38) Voisin, P., Namboodiri, M. A. A., Klein, D. C. (1984) Arylamine N-acetyltransferase and arylalkylamine N-acetyltransferase in the mammalian pineal gland. *J. Biol. Chem.* 259, 10913–10918.
39) Klein, D. C., Weller, J. L. (1970) Indole metabolism in the pineal gland, a circadian rhythm in N-acetyltransferase. *Science* 169, 1093–1095.
40) Klein, D. C., Roseboom, P. H., & Coon, S. L. (1996) New light is shining on the melatonin rhythm enzyme. The first postcloning view. *Trends Endocrinol. Metab.* 7, 106–112.
41) Coon, S. L., Roseboom, P. H., Baler, R., Weller, J. L., Namboodiri, M. A. A., Koonin, E. V., Klein, D. C. (1995) Pineal serotonin N-acetyltransferase: expression cloning and molecular analysis. *Science* 270, 1681–1683.
42) Borjigin, J., Wang, M. M., Snyder, S. H. (1995) Diurnal variation in mRNA encoding serotonin N-acetyltransferase in pineal gland. *Nature* 378, 783–785.
43) Ishida, I., Obinata, M., & Deguchi, T. (1987) "Molecular cloning and nucleotide sequence of cDNA encoding hydroxyindole O-methyltransferase of bovine pineal glands" *J. Biol. Chem.* 262, 2895–2899.
44) Axelrod, J. (1974) The pineal gland: a neurochemical transducer. *Science* 184, 1341–1348.
45) Klein, D. C., Coon, S. L., Roseboom, P. H., Weller, J. L., Bernard, M., Gastel, J. A., Zatz, M., Iuvone, P. M., Rodriquez, I. R., Begay, V., Falcon, J., Cahill, G. M., Cassone, V. M., and Baler, R. (1997) The melatonin rhythm-generating enzyme: molecular regulation of serotonin N-acetyltransferase in the pineal gland. *Recent Progress in Hormone Research* 52, 307–357.

46) Coon, S. L., Mazuruk, K., Bernard, M., Roseboom, P. H., Klein, D. C., & Rodriguez, I. R. (1996) The human serotonin N-acetyltransferase (EC 2.3.1.87) gene (AANAT): structure, chromosomal localization, and tissue expression. *Genomics* 34, 76–84.

47) Datla, K. P., Curzon, G. (1996) Effect of p-chlorophenylalanine at moderate dosage on 5-HT and 5-HIAA concentrations in brain regions of control and p-chloroamphetamine treated rats. *Neuropharmacology* 35, 315–320.

48) Hudgel, D. W., Gordon, E. A., (1997) Serotonin-induced cortisol release in CPAP-treated obstructive sleep apnea patients. *Chest* 111, 632–638.

49) Satake. N., Morton, B. (1979) Pineal hydroxyindole-O-methyltransferase: mechanism and inhibition by scotophobin A. *Pharmacology, Biochemistry & Behavior* 10, 457–462.

50) Yang, X.-J., Ogrryzko, V. V., Nishikawa, J., Howard, B. H., Nakatani, Y. (1996) A p300/CBP-associated factor that competes with the adenoviral oncoprotein E1A *Nature* 382, 319–324.

51) DeAngelis, J., Gastel, J., Klein, D. C., Cole, P. A. (1998) Kinetic Analysis of the Catalytic Mechanism of Setotonin N-Acetyltransferase *J. Biol. Chem.* 273, in press.

52) Deguchi, T. (1975) Characteristics of serotonin-acetyl coenzyme A N-acetyltransferase in pineal gland of rat *J. Neurochem.* 24, 1083–1085.

53) Shaw, W. V., & Leslie, A. G. W. (1991) Chloramphenicol acetyltransferase. *Annu. Rev. Biophys. Biophys. Chem.* 20, 363–386.

54) Colucci, W. J., Gandour, R. D. (1988) Carnitine acetyltransferase: a review of its biology, enzymology, and bioorganic chemistry. *Bioorganic Chemistry* 16, 307–334.

55) Grant, D. M., & Dupret, J.-M. (1992) Site-directed mutagenesis of recombinant human arylamine N-acetyltransferase expressed in *Escherichia coli*. *J. Biol. Chem.* 267, 7381–7385.

56) Schuberth, J. (1966) Choline acetyltransferase. Purification and effect of salts on the mechanism of the enzyme-catalyzed reaction. *Biochim. Biophs. Acta* 122, 470–481.

57) Roskoski, R. (1973) Choline acetyltransferase. Evidence for an acetyl-enzyme reaction intermediate. *Biochemistry* 12, 3709–3714.

58) Wolfe, M. S., Lee, N. R., Zatz, M. (1995) Properties of clock-controlled and constitutive N-acetyltransferases from chick pineal cells. *Brain Research* 669, 100–106.

59) Morrissey, J. J., Edwards, S. B., & Lovenberg, W. (1977) Comparison of rat pineal gland and rat liver serotonin-N-acetyltransferase. *Biochem. Biophys. Res. Commun.* 77, 118–123.

60) Segel. I. H. (1975) 'Enzyme Kinetics', Wiley-Interscience, New York.

61) Kayumov, V., Smushkevich, Y. I., Suvorov, N. N. (1973) Preparation of indolylalkylamines by the reduction of hydroxmiac acids. *Zh. Vses. Khim. Obschchest.* 18, 342.

62) Kitaguchi, H., Fitzpatrick, P. A., Huber, J. E., Klibanov, A. M. (1989) Enzymatic resolution of racemic amines. Crucial role of the solvent. *J. Am. Chem. Soc.* 111, 3094–3095.

63) Walsh, C. T. (1983) Fluorinated substrate analogs: routes of metabolism and selective toxicity. *Adv. Enzymol,* 55, 197–289.

64) Zimmer, R., Reissig, H.-U. (1992) Efficient synthesis of trifluoromethyl-substituted 5,6-dihydro-4H-1,2-oxazines by the hetero-Diels-Alder reaction of 1,1,1-trifluoro-2-nitroso-2-propene and electron rich olefins. *J. Org. Chem.* 57, 339–347.

65) Kim, K. and *Cole, P. A.* (1997) Measurement of a Bronsted Nuceophile Coefficient and Insights into the Transition State for a Protein Tyrosine Kinase *J. Am. Chem. Soc.* 119, 11096–11097.

66) Cole, P. A., Burn, P., Takacs, B., Walsh, C. T. (1994) Evaluation of the catalytic mechanism of Csk (C-terminal Src kinase) using nucleotide analogs and viscosity effects. *J. Biol. Chem.* 269, 30880–30887.

67) Wolfenden, R. (1969) Transition state analogues for enzyme catalysis. *Nature* 223, 704–705.

68) Chase, J. F. A., Tubbs, P. K. (1969) Conditions for the Self-catalysed inactivation of carnitine acetyltransferase. *Biochem. J.* 111, 225–235.

69) Cullis, P. M., Wolfenden, R., Cousens, L. S., Alberts, B. M. (1982) Inhibition of histone acetylation by N-[2-(S-Coenzyme A)acetyl] spermidine amide, a multisubstrate analog. *J. Biol. Chem.* 257, 12165–12169.

70) Wagner, G. (1997) An account of NMR in structural biology. *Nat. Struct. Biol.* 4S, 841–844.

71) Studier, F. W., Rosenberg, A. H., Dunn, J. J., Dubendorf, J. W. (1990) Use of T7 RNA polymerase to direct expression of cloned genes. *Methods Enz.* 185, 60–89.

72) Cole, P. A. (1996) Chaperone-assisted protein expression. *Structure* 4, 239–242.

73) Grace, M. R., Walsh, C. T., *Cole, P. A.* (1997) Divalent Ion Effects and Insights into the Catalytic Mechanism of Protein Tyrosine Kinase Csk *Biochemistry* 36, 1874–1881.

74) Chong, S., Mersha, F. B., Comb, D. G., Scott, M. E., Landry, D., Vence, L. M., Perler, F. B., Benner, J., Kucera, R. B., Hirvonen, C. A., Pelletier, J., Paulus, H., Xu, M.-Q. (1997) *Gene* 192, 271–281.

75) Muir, T. W., Sondhi, D., Cole, P. A. (1997) Expressed Protein Ligation: A General Method for Protein Engineering, manuscript submitted.

76) Cohen, S. L., Ferre-D'Amare, A. R., Burley, S. K., Chait, B. T. (1995) Probing the solution structure of the DNA-binding protein Max by a combination of proteolysis and mass spectrometry. *Protein Science* 4, 1088–1099.

77) Cohen, S. L. (1996) Domain elucidation by mass spectrometry. *Structure* 4, 1013–1016.

78) Ferre-D'Amare, A. R., Burley, S. K. (1997) Dynamic light-scattering as a tool for evaluating crystallizability of macromolecules. *Meth. Enz.,* 276, 157–166.

79) Lakowicz, J. R. (1983) 'Principles of fluorescence spectroscope.' Plenum Press, New York.

80) Lakowicz, J. R., ed (1991) 'Topics in fluorescence spectroscope.' Plenum Press, New York.

81) Cantor. C. R., Schimmel, P. R. (1971) 'Biophysical Chemistry'. W. H. Freeman, New York.

82) Doyle, M. L. (1997) Characterization of binding interactions by isothermal titration calorimetry. *Current Opinion in Biotechnology* 8, 31–35.

83) Wiseman, T., Williston, S., Brandts, J. F., Lin, L.-N. (1989) Rapid measurement of binding constants and heats of binding using a new titration calorimeter. *Anal. Biochem.* 179, 131–137.

84) Myszka, D. G. (1997) Kinetic analysis of macromolecular interactions using surface plasmon resonance biosensors. *Current Opinion in Biotechnology* 8, 50–57.

85) Meikle, P. J., Whittle, A. M., Hopwood, J. J. (1995) Human acetyl-coenzyme A: a-glucosaminide N-acetyltransferase. Kinetic characterization and mechanistic interpretation. *Biochem. J.* 308, 327–333.

86) Jencks, W. P. (1969) Catalysis in chemistry and enzymology. McGraw-Hill, New York.

87) Bollinger, J. M Jr., Kwon, D. S., Huisman, G. W., Kolter, R., Walsh, C. T. (1995) Glutahionylspermidine metabolism in *Escherichia coli*. Purification, cloning, overproduction, and characterization of a bifunctional glutathionylspermidine synthetase/amidase. *J. Biol. Chem.* 270, 14031–14041.
88) Dixon, M., Webb, E. C. (1964) 'Enzymes.' Academic Press, New York.
89) Hess, R. A., Hengge, A. C., Cleland, W. W. (1997) Kinetic isotope effects for acyl transfer from p-nitrophenyl acetate to hydroxylamine show a pH-dependent change in mechanism. *J. Am. Chem., Soc.* 119, 6980–6983.
90) Cook, P. F., ed. (1991) 'Enzyme mechanisms from isotope effects.' CRC Press, Boca Raton, Fla.
91) Cleland, W. W., O'Leary, M. H., Northrop, D. B., eds (1977) 'Isotope effects on enzymatic catalyzed reactions.' University Park Press, Baltimore.
92) Hennge, A. C., Hess, R. A. (1994) Concerted or stepwise mechanisms for acyl transfer reactions of p-nitrophenyl acetate? Transition state structures from isotope effects. *J. Am. Chem. Soc.* 116, 11256–11263.
93) Lai, M.-t., Li, D., Oh, E., Liu, H.-w. (1993) Inactivation of medium-chain acyl-CoA dehydrogenase by a metabolite of hypoglycin: characterization of the major turnover product and evidence suggesting an alternative flavin modification pathway. *J. Am. Chem. Soc.* 115, 1619–1628.
94) Battersby, A. R., Gutman, A. L., Fookes, C. J. R., Gunther, H., Simon (1981) Stereochemistry of formation of methyl and ethyl groups in bacteriochlorophyll a. *J. Chem. Soc., Chem. Commun.* 645–647.
95) Welch, J. T., Eswarakrishnan, S. (1991) Fluorine in bioorganic chemistry. Wiley, New York.
96) Matulic-Adams, J., Takhashi, K., Chou, T. C., Gadler, H., Price, R. W., Reddy, A. R. V., Kalman, T. i., Watanbe, K. A. (1988) *J. Med. Chem.* 31, 1642–1647.
97) March, J. (1985) 'Advanced organic chemistry.' Wiley, New York.
98) Stivers, J. T., Abeygunawardana, C., Mildvan, A. S., Hajipour, G., Whitman, C. P., Chen, L. H. (1996) *Biochemistry* 35, 803–813.
99) Stivers, J. T., Abeygunawardana, C., Mildvan, A. S., Hajipour, G., Whitman, C. P. (1996) *Biochemistry* 35, 814–823.
100) Cho, H., Ravichandran, K., Kitas, E., Bannwarth, W., Walsh, C. T., Anderson, K. S. (1992) Isolation and structural elucidation of a novel phosphocysteine intermediate in the LAR protein tyrosine phosphatase enzymatic pathway. *J. Am. Chem. Soc.* 114, 7296–7298.
101) Kyte, J. (1995) 'Mechanism in protein chemistry'. Garland, N.Y. 314–336.
102) Lu, L., Berkey, K. A., Casero, R. A. (1996) RGFGIGS is an amino acid sequence required for acetyl coenzyme A binding and activity of human spermidine/spermine N1-acetyltransferase *J. Biol. Chem.* 271, 18920–18924.
103) Javier Teran, F., Alvarez, M., Suarez J. E., Mendoza, M. C. (1991) Characterization of two aminoglycoside-(3)-N-acetyltransferase genes and assay as epidemiological probes. *Journal of Antimicrobial Chemotherapy* 28, 333–46.
104) Morrison, J. F., Walsh, C. T. (1988) The behavior and significance of slow-binding enzyme inhibitors. *Adv. Enzymol.* 61, 201–301.
105) Robishaw, J. D., Neely, J. R. (1985) Coenzyme A metabolism. *Am J. Physiol.* 248, E1–E9.
106) Spector, R. (1986) Pantothenic acid transport and metabolism in the central nervous system. *Am J. Physiol.* 250, R292–R297.
107) Spector, R. (1986) Development and characterization of pantothenic acid transport in brain. *J. Neurochem.* 47, 563–568.
108) Shimizu, M., Abiko, Y. (1965) Investigations on pantothenic acid and its related compounds. II. Biochemical studies. (1) Biosynthesis of coenzyme-A from pantothenate, pantetheine and from S-benzoylpantetheine in vitro and in vivo. *Chem. Pharm. Bull,* 13, 189–198.
109) Tahiliani, A. G. (1991) Evidence for net uptake and efflux of mitochondrial coenzyme A. *Biochim. Biophys. Acta* 1067, 29–37.
110) Nguyen, T.-G., Gerbing, K., Eggerer, H. (1984) New susbtrates and inhibitors of 3-hydroxy-3-methylglutaryl-CoA. *Hoppe-Seyler's Z. Physiol. Chem.* Bd. 365, 1–8.

What is claimed is:

1. A compound represented by formula I.

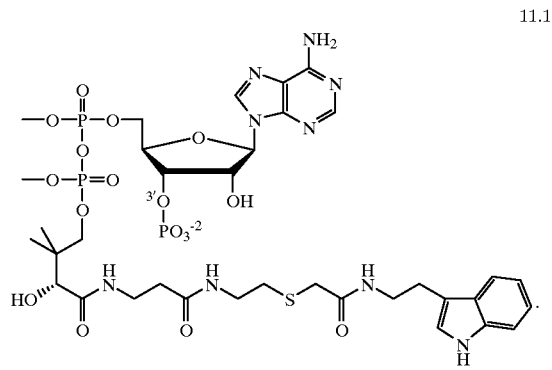

2. A compound represented by formula II.

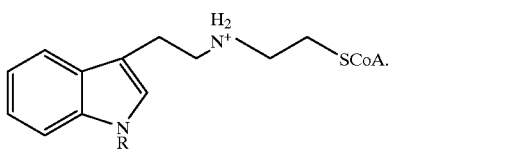

3. A compound represented by formula III.

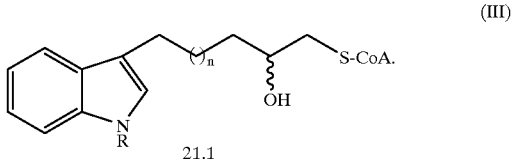

4. A compound represented by formula IV.

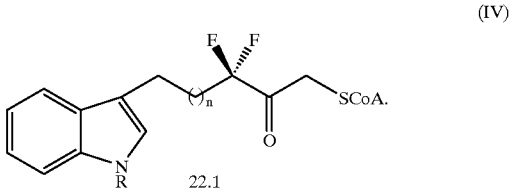

5. A pharmaceutical composition comprising the serotonin N-acetyltransferase inhibitor of any one of claims 1–4 and a pharmaceutically acceptable carrier.

6. A method of inhibiting serotonin N-acetyltransferase comprising administering to a subject the pharmaceutical composition of claim 5 in an effective amount so as to inhibit serotonin N-acetyltransferase.

* * * * *